US012710430B2

(12) United States Patent
Yang et al.

(10) Patent No.: US 12,710,430 B2
(45) Date of Patent: Aug. 18, 2026

(54) LAMA2, PLXDC2 AND MLL4 AS NOVEL BIOMARKERS FOR PREDIABETES AND DIABETES

(71) Applicant: Academia Sinica, Taipei City (TW)

(72) Inventors: Wen-Chin Yang, Taichung County (TW); Meng-Ting Yang, New Taipei City (TW)

(73) Assignee: ACADEMIA SINICA, Taipei City (TW)

( * ) Notice: Subject to any disclaimer, the term of this patent is extended or adjusted under 35 U.S.C. 154(b) by 1058 days.

(21) Appl. No.: 17/611,155

(22) PCT Filed: May 12, 2020

(86) PCT No.: PCT/US2020/032543
§ 371 (c)(1),
(2) Date: Nov. 14, 2021

(87) PCT Pub. No.: WO2020/232034
PCT Pub. Date: Nov. 19, 2020

(65) Prior Publication Data

US 2022/0206014 A1 Jun. 30, 2022

Related U.S. Application Data

(60) Provisional application No. 62/849,118, filed on May 16, 2019.

(51) Int. Cl.
*G01N 33/68* (2006.01)
*G01N 33/543* (2006.01)

(52) U.S. Cl.
CPC ... *G01N 33/6893* (2013.01); *G01N 33/54388* (2021.08); *G01N 2800/042* (2013.01)

(58) Field of Classification Search
CPC ............. G01N 2800/042; G01N 31/22; G01N 33/54388; G01N 33/6893
See application file for complete search history.

(56) References Cited

U.S. PATENT DOCUMENTS

2010/0167264 A1 7/2010 Lee
2010/0196426 A1 * 8/2010 Skog .................... C12Q 1/6883 604/7

OTHER PUBLICATIONS

Anfossi et al., "Multiplex Lateral Flow Immunoassay: An Overview of Strategies towards High-throughput Point-of-Need Testing," Biosensors (Basel), Dec. 26, 2018; 9(1):2, pp. 1-14.*
Torné-Morató et al., "Sensitivity-enhanced competitive lateral flow immunoassays by polycaprolactone electrospun stacking pad: Estrous determination in whole blood," Biosensors Bioelectronics, 2025, vol. 271, 117080, pp. 1-8.*
Yang et al., "Identification of Novel Biomarkers for Pre-diabetic Diagnosis Using a Combinational Approach," Front. Endocrinol., Apr. 27, 2021, vol. 12, Article 641336, pp. 1-12.*
International Search Report for PCT/US2020/032543, dated Aug. 26, 2020.
Written Opinion of International Search Authority for PCT/US2020/032543, dated Aug. 26, 2020.
Lehti et al. "Effects of streptozotocin-induced diabetes and physical training on gene expression of extracellular matrix proteins in mouse skeletal muscle" Am J Physiol Endocrinol Metab 290: E900-E907, 2006.
Zhang et al."Identifying module biomarker in type 2 diabetes mellitus by discriminative area of functional activity" BMC Bioinformatics (2015) 16:92.
Michelsen et al "Investigation of Archived Formalin-Fixed Paraffin-Embedded Pancreatic Tissue withWhole-Genome Gene ExpressionMicroarray" Intemational Scholarly Research Network ISRN Pathology vol. 2011, Article ID 275102, 12 pages.

* cited by examiner

*Primary Examiner* — Galina M. Yakovleva
(74) *Attorney, Agent, or Firm* — Hsiu-Ming Saunders; IPC INTELLECTUAL PROPERTY CONNECTIONS, INC.

(57) ABSTRACT

The invention relates to LAMA2, PLXDC2 and MLL4 as novel biomarkers for prediabetes and diabetes. Specifically, use of a set of probes with specific binding affinities to prediabetes and diabetes protein markers comprising MLL4, LAMA2, and PLXDC2 for screening prediabetes and diabetes for care and/or treatment is disclosed. The set of probes comprises a first probe, a second probe and a third probe having specific binding affinities to the MLL4, LAMA2, and PLXDC2, respectively. A diagnostic kit device/apparatus comprising a set of probes is disclosed. A method for detecting and identifying prediabetes and/or diabetes in a subject in need thereof is also disclosed. The subject in need thereof identified as having prediabetes or diabetes is subject to a care and/or a treatment regime for the prediabetes or diabetes. Also disclosed is a method for identifying prediabetes and/or diabetes protein markers.

8 Claims, 5 Drawing Sheets

Specification includes a Sequence Listing.

FIG. 1

Discovery

Health (n=3)

Pre-diabetes (n=3)

114

115 116 117

Protein labeling by iTRAQ

Labeled peptide pooling

SCX chromatography

LC-MS/MS

Mascot analysis

Discovery

Health (n=3)

Pre-diabetes (n=3)

114

115 116 117

Protein labeling by iTRAQ

Labeled peptide pooling

SCX chromatography

LC-MS/MS

Mascot analysis

The intersection analysis of mice and humans proteins

Ratio and *P* value analysis for human total proteins

Transformed volcano plot analysis

Potential markers selection

Validation

Gene ontology

Potential markers network

Candidate proteins for T2D markers

Western blot

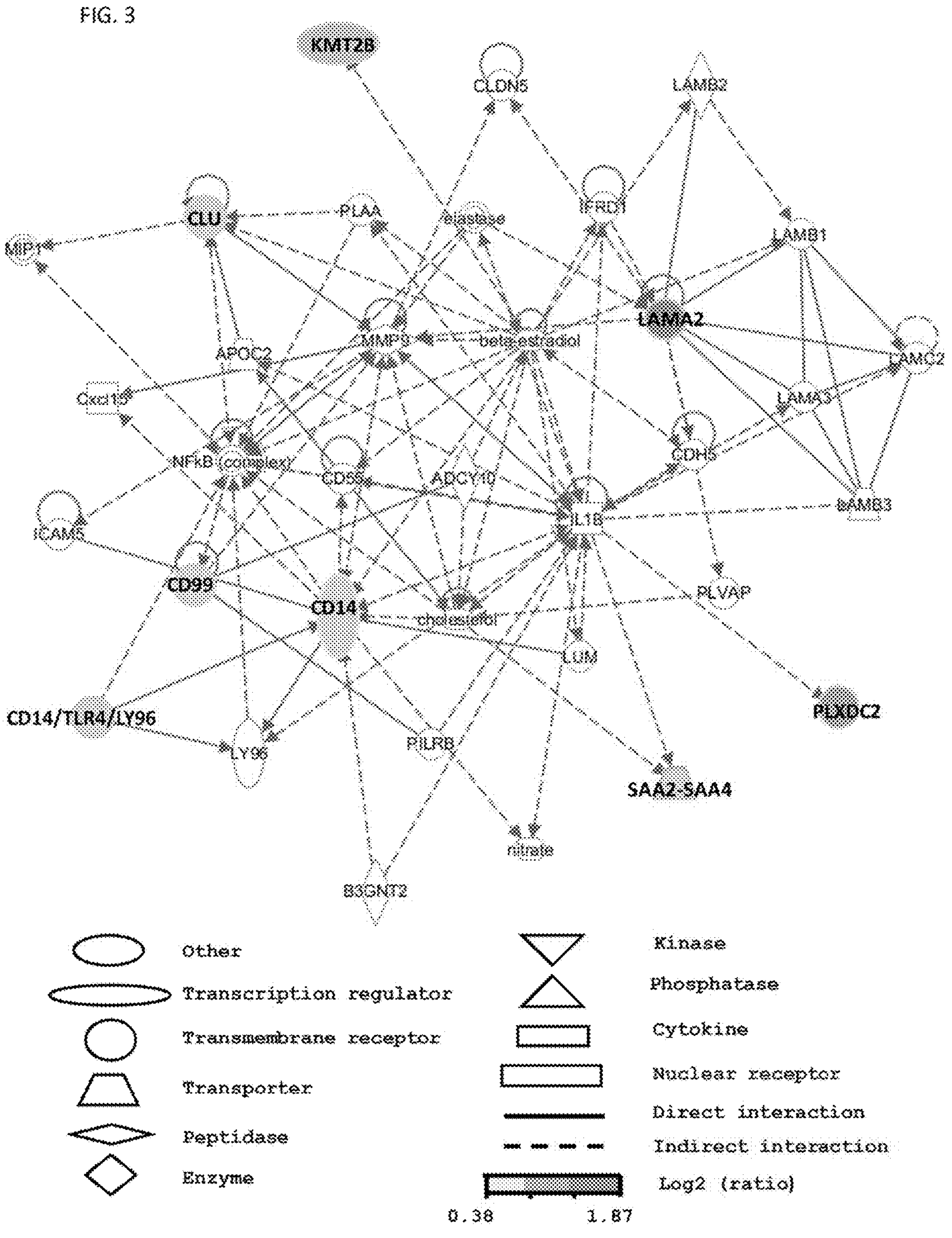
FIG. 3
KMT2B
CLDN5
LAMB2
CLU
PLAA
elastase
IFRD1
LAMB1
MIP1
LAMA2
MMP9
beta-estradiol
APOC2
LAMC2
Cxcl15
LAMA3
CDH5
NFkB (complex)
CD55
ADCY10
LAMB3
ICAM5
IL1B
CD99
PLVAP
CD14
cholesterol
LUM
CD14/TLR4/LY96
PLXDC2
LY96
PILRB
SAA2-SAA4
nitrate
B3GNT2
Other
Transcription regulator
Transmembrane receptor
Transporter
Peptidase
Enzyme
Kinase
Phosphatase
Cytokine
Nuclear receptor
Direct interaction
Indirect interaction
Log2 (ratio)
0.38
1.87

A

Healthy 1 2 3 4 5 — Pre-T2D 1 2 3 4 5

211KD LAMA2
72KD MLL4
93KD PLXDC2
66KD Transferrin

B

Sensitivity

Lama2, AUC=0.9257
PLXDC2, AUC=0.91445
MLL4, AUC= 0.95795
Lama2+PLXDC2+MLL4, AUC: 0.95795

C

| Biomarkers | AUC | Sensitivity | Specificity | Accuracy |
|---|---|---|---|---|
| Lama2 | 0.9275 | 71.42% | 71.42% | 71.42% |
| PLXDC2 | 0.91445 | 71.42% | 71.42% | 71.42% |
| MLL4 | 0.95795 | 71.42% | 71.42% | 71.42% |
| Lama2 +PLXDC2 +MML4 | 0.95795 | 71.42% | 71.42% | 71.42% |

D

FIG. 5
A
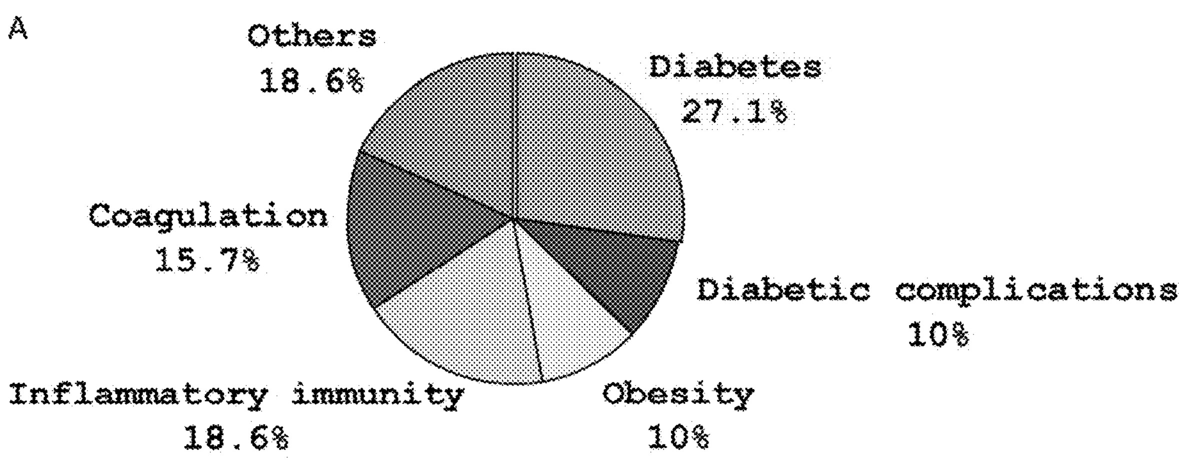
B
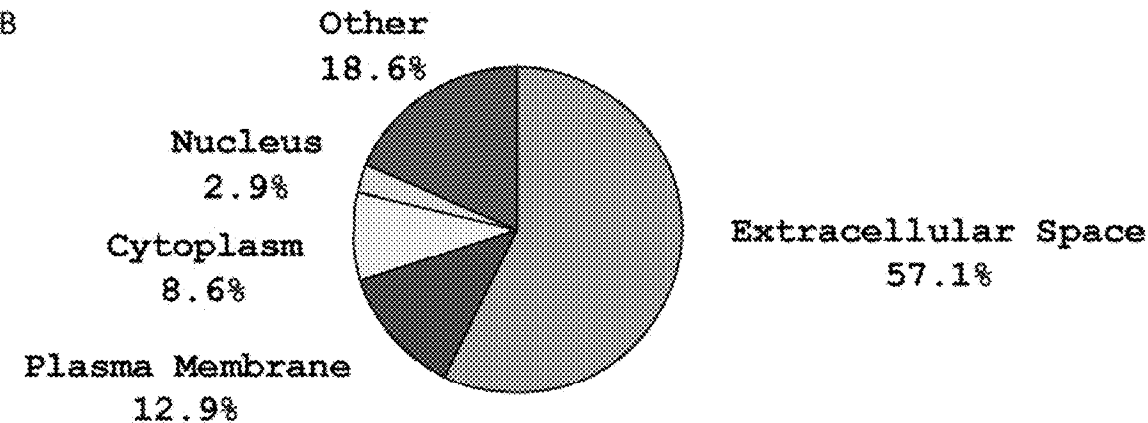
C
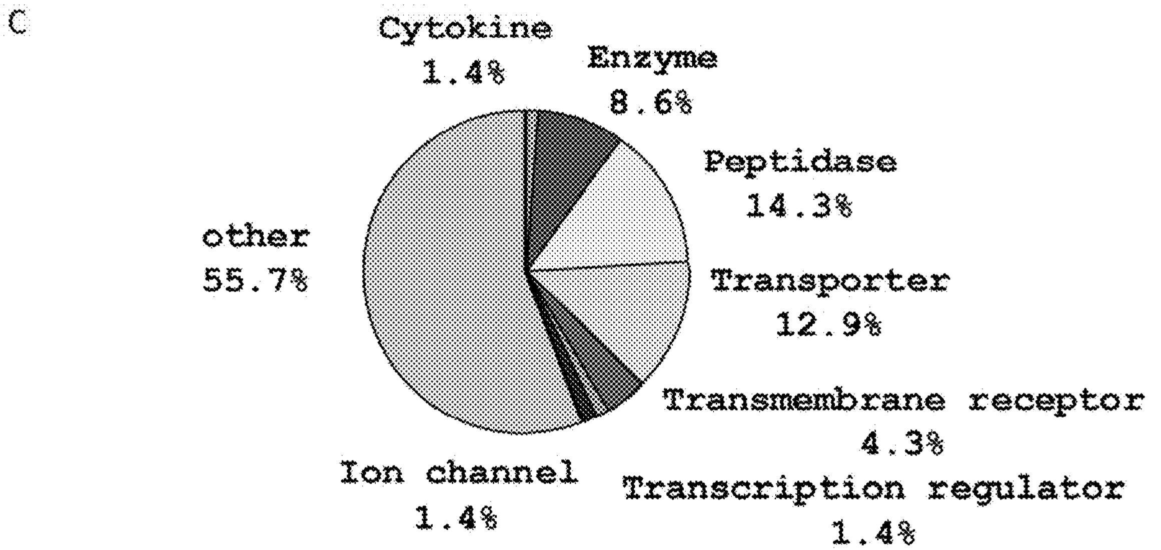

LAMA2, PLXDC2 AND MLL4 AS NOVEL BIOMARKERS FOR PREDIABETES AND DIABETES

REFERENCE TO RELATED APPLICATION

This application is a national stage application (under 35 U.S.C. 371) of PCT/US2020/032543 filed 12 May 2020, which claims priority to US provisional application 62/849,118 filed on 16 May 2019, all of which are herein incorporated by reference in their entireties.

FIELD OF THE INVENTION

The present invention relates generally to protein markers for use in detecting (pre)diabetes, and more specifically to use of LAMA2. PLXDC2 and MLL4 for detecting, preventing and treating prediabetes and diabetes.

BACKGROUND OF THE INVENTION

Diabetes is a life-threatening metabolic disease characterized by hyperglycemia and poorly regulated carbohydrate metabolism resulting from insulin resistance and/or β-cell dysfunction. Despite several improvements and advances in type 2 diabetes (T2D) diagnosis and therapy over the past years, it is still an incurable disease. Accumulating evidence suggests that prevention is better than treatment because early prevention and intervention can significantly reduce the incidence of T2D and its complications. For instance, diet control, exercise and bariatric surgery prevented T2D in high-risk subjects. Prophylaxis with metformin also decreased the incidence of T2D. Therefore, identification of subjects at high risk for T2D before its clinical onset holds the key to prevention of the disease.

Many efforts have been made to identify genetic and protein markers for T2D. Although genetic markers have high reliability, they are not satisfactory because they show up at T2D rather than prediabetes stage and have modest sensitivity and specificity. On the other hand, protein markers have high sensitivity and specificity because they reflect the progression of the disease systematically and dynamically. Moreover, protein levels are tightly regulated by cellular stimulation. Thus, protein markers are potentially useful for diagnosis.

SUMMARY OF THE INVENTION

In one aspect, the invention relates to a diagnostic kit for detecting and identifying prediabetes and/or diabetes, comprising (i) a substrate having a top surface and a bottom surface opposite to the top surface, and a top end and a bottom end opposite to the top end; (ii) a sample loading area; (iii) a capture antibody area, containing capture antibodies to capture prediabetes and diabetes protein markers comprising MLL4, LAMA2, and PLXDC2; (iv) a reagent area, containing a conditioning reagent; (v) a detection antibody area, containing detection antibodies to detect the captured prediabetes and diabetes protein markers comprising the MLL4, LAMA2, and PLXDC2; and (vi) optionally a positive control area; wherein the sample loading area, the detection antibody area, the reagent area, the capture antibody area, and the positive control area are located on the top surface of the substrate, allowing these areas to be in fluidic communication, the sample loading area being located at the top end and the capture antibody area located at the bottom end with the optionally positive control area located either after or before the capture antibody area.

In one embodiment, the capture antibody area contains capture antibodies to capture one or more additional prediabetes and diabetes protein markers besides the MLL4, LAMA2, and PLXDC2.

In another embodiment, the diagnostic kit may further comprise (vii) an instruction sheet showing directions of performing a method of detecting and identifying prediabetes and/or diabetes according to the method invention.

The conditioning reagent may comprise a buffer solution, a detergent, a protease inhibitor, a salt, and/or a divalent cation. The reagent area may further comprise a color-forming reagent and a conditioning reagent.

In one embodiment, the capture antibodies, the conditioning reagent and the detection antibodies are coated onto the top surface of the substrate. The substrate may be a nitrocellulose membrane.

In another embodiment, the diagnostic kit device/apparatus of the invention is optimized for performance by lateral flow immunoassay.

In another aspect, the invention relates to a method for detecting and identifying prediabetes and/or diabetes, comprising (a) providing the diagnostic kit of the invention; (b) supplying a serum sample from a subject in need thereof; and (c) detecting whether the levels of prediabetes and diabetes protein markers comprising MLL4, LAMA2, and PLXDC2 in the serum sample are increased as compared with a healthy control, wherein an increase in the levels of the protein markers MLL4, LAMA2, and PLXDC2 is indicative of the subject in need thereof having prediabetes or diabetes.

Further in another aspect, the invention relates to a method for detecting and identifying prediabetes and/or diabetes, comprising (a) supplying a serum sample from a subject in need thereof; and (b) detecting whether the levels of prediabetes and diabetes protein markers comprising MLL4, LAMA2, and PLXDC2 in the serum sample are increased as compared with a healthy control, wherein an increase in the levels of the protein markers MLL4, LAMA2, and PLXDC2 is indicative of the subject in need thereof having prediabetes or diabetes.

In one embodiment, the levels of the protein markers MLL4, LAMA2 and PLXDC2 exhibiting an area under an Receiver Operating Characteristic (ROC) curve of greater than 0.91 is indicative of the subject in need thereof having prediabetes or diabetes.

In another embodiment, the levels of the protein markers MLL4, LAMA2 and PLXDC2 exhibiting an area under the ROC curve of greater than 0.95 is indicative of the subject in need thereof having prediabetes or diabetes.

In another embodiment, the prediabetes and diabetes protein markers may further comprise one or more additional prediabetes and diabetes protein markers.

The detecting step may further comprise (d) providing capture antibodies specific against the MLL4, LAMA2, and PLXDC2, to form captured protein markers MLL4, LAMA2, and PLXDC2, respectively; (e) affording a conditioning reagent; and (f) supplying detection antibodies specific against the captured protein markers MLL4, LAMA2, and PLXDC2, respectively.

The supplying step may further comprise the step of providing a diagnostic kit for detecting and identifying prediabetes and/or diabetes, in which the diagnostic kit comprises: (i) a substrate having a top surface and a bottom surface opposite to the top surface, and a top end and a bottom end opposite to the top end; (ii) a sample loading area; (iii) a capture antibody area, containing capture antibodies to capture prediabetes and diabetes protein markers comprising MLL4, LAMA2, and PLXDC2; (iv) a reagent area, containing a conditioning reagent; (v) a detection antibody area, containing detection antibodies to detect the captured prediabetes and diabetes protein markers comprising the MLL4, LAMA2, and PLXDC2; and (vi) optionally a positive control area; wherein the sample loading area, the detection antibody area, the reagent area, the capture antibody area, and the positive control area are located on the top surface of the substrate, allowing these areas to be in fluidic communication, the sample loading area being located at the top end and the capture antibody area located at the bottom end with the optionally positive control area located either after or before the capture antibody area.

In another embodiment, the detecting step may be performed by visualizing a color change.

The capture antibodies and detection antibodies may be polyclonal antibodies. In another embodiment, the capture antibodies and detection antibodies are monoclonal antibodies. Further in another embodiment, the capture antibodies are polyclonal antibodies and detection antibodies are monoclonal antibodies, or vice versa.

In another embodiment, the detection antibodies are labeled with colloidal gold, or a color-generating enzyme, and the conditioning reagent comprises a substrate for the color-generating enzyme.

In another embodiment, the method is performed by a lateral flow immunoassay.

The invention further relates to use of a set of probes for detecting and identifying prediabetes and/or diabetes in a patient.

Further in another aspect, the invention relates to use of a set of probes with specific binding affinities to prediabetes and diabetes protein markers comprising MLL4, LAMA2, and PLXDC2 in the manufacture of the diagnostic kit for detecting prediabetes and/or diabetes of the invention.

The set of probes comprises (a) a first probe having a specific binding affinity to the MLL4; (b) a second probe having a specific binding affinity to the LAMA2; and (c) a third probe having a specific binding affinity to the PLXDC2.

In another aspect, the invention relates to use of a set of probes with specific binding affinities to prediabetes and diabetes protein markers comprising MLL4, LAMA2, and PLXDC2 in the manufacture of a diagnostic kit for detecting prediabetes and/or diabetes, wherein the set of probes comprises (a) a first probe having a specific binding affinity to the MLL4; (b) a second probe having a specific binding affinity to the LAMA2; and (c) a third probe having a specific binding affinity to the PLXDC2.

In another embodiment, the use of the set of the probes further comprise use of conditioning reagents, and a substrate in the manufacture of the diagnostic kit for detecting prediabetes and/or diabetes of the invention.

The set of probes may further comprise one or more additional probes with specific binding affinities to prediabetes and diabetes protein markers other than the MLL4, LAMA2, and PLXDC2.

In another embodiment, the probes are antibodies comprising capture antibodies and detection antibodies.

Moreover, the invention relates to screening prediabetes and diabetes for care and/or treatment.

Yet in another aspect, the invention relates to a method for care and treatment of prediabetes and/or diabetes, comprising the steps of: (I) detecting and identifying prediabetes and/or diabetes in a subject in need thereof; and (II) subjecting the subject in need thereof being identified as having the prediabetes or diabetes to a care and/or treatment regime for the prediabetes or diabetes. The detecting and identifying step further comprises: (a) supplying a serum sample from a subject in need thereof; and (b) detecting whether the levels of prediabetes and diabetes protein markers comprising MLL4, LAMA2, and PLXDC2 in the serum sample are increased as compared with a healthy control, wherein an increase in the levels of the protein markers MLL4, LAMA2, and PLXDC2 is indicative of the subject in need thereof having prediabetes or diabetes.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIG. 1 is a flow chart indicating the experimental designs for discovery of serum proteins of mouse and human origins, followed by validation of their presence in human sera. Serum samples were collected from 3 healthy mice/volunteers and 3 prediabetic mice/patients with 16 and 12 hrs of fasting. Serum from 3 heathy mice were pooled together and labeled with iTRAQ® 114. Serum from 3 prediabetic mice were labeled with iTRAQ® 115, 116 and 117, respectively. Subsequently, four of them were pooled together for iTRAQ®-based discovery. The same experimental processing was applied to human samples for iTRAQ®-based discovery. The proteins with high confidence (average relative ratio and p value) and novelty were selected as potential markers for immunoblotting validation.

FIG. 3 shows pathway analysis of the selected serum proteins from human sera using IPA®. The network is related to connective tissue disorders, dermatological diseases and conditions and developmental disorders. The markers which increased in prediabetic mice and patients were labelled in red color.

FIG. 5 shows pie charts of gene ontology for biological process (A), molecular functions (B) and cellular components (C) of the selective serum proteins with statistical significance ($P<0.05$) in prediabetic patients compared to healthy volunteers.

DETAILED DESCRIPTION OF THE INVENTION

Definitions

Figure 2:
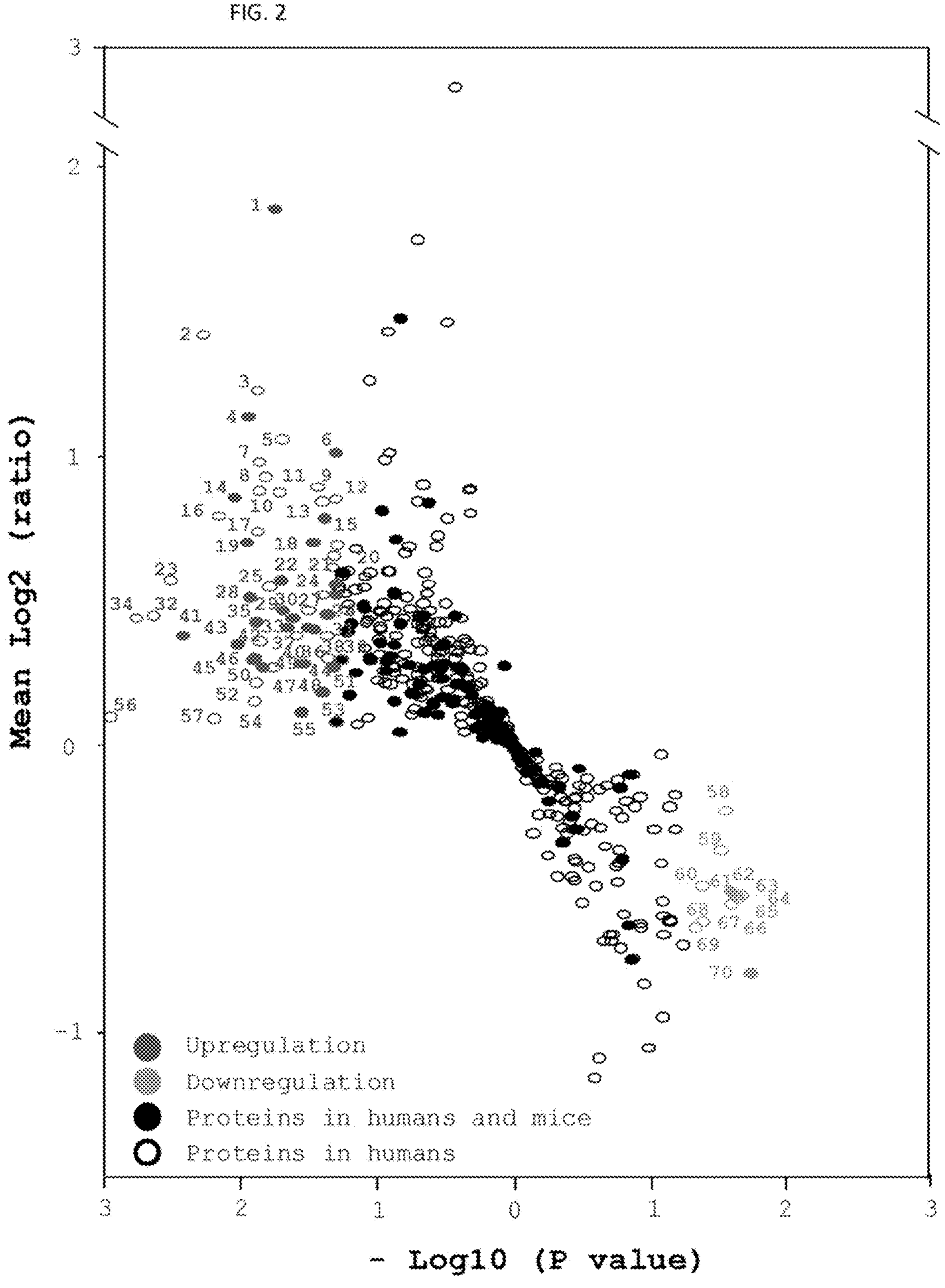
FIG. 2 shows transformed volcano plot analysis of the selected proteins from human sera. Total proteins from human sera were processed using a combination of iTRAQ® and mass spectrometry (MS), followed by Mascot software identification. A transformed volcano plot was used to analyze log 2 (ratio of the level of one serum protein in prediabetic patient to its average level in healthy subjects). The serum proteins, detected in human and mouse sera, are labelled by solid dots. The ones, only detected in humans, are labelled by hollow dots. Up-regulated and down-regulated proteins with P<0.05 (*) were labelled by red and green colors, respectively. The proteins with P<0.01 (**) and average expression ratio over 1.3 were selected for further analysis using INGENUITY® Pathway Analysis (IPA®). Student's t-test was used to compare the differences between heathy and prediabetic mice and humans.

As used herein, the term "(pre)diabetes" shall generally mean both prediabetes and diabetes.

The term "a healthy control" shall generally mean a healthy subject who is neither a prediabetes nor a diabetes.

As used herein, a diagnostic kit shall mean a set or collection of (pre)-diabetes protein markers for diagnosis of prediabetes and/or diabetes, or a set or collection of (pre)-diabetes protein markers from which a diagnostic kit device/apparatus can be assembled, or shall mean a diagnostic kit device/apparatus that contain such a set or collection of (pre)-diabetes protein markers.

The term "a reagent area", exchangeable with "a reagent depot", shall generally mean a region containing "conditioning reagents".

The term "conditioning reagents" means reagents that are required to optimize the detection or assay method.

The term "detection antibodies" shall generally mean antibodies specific against prediabetes and diabetes protein markers, which are conjugated to either an enzyme or other molecule to visualize the binding reaction of protein markers to captured antibodies.

The term "capture antibodies" shall generally mean antibodies specific against prediabetes and diabetes protein markers. A capture antibody captures a protein marker by specific binding to the protein marker.

The terms "capture antibody area" and "a test reading area" are interchangeable.

The term "a care and/or treatment regime" shall generally mean a medicine or medical regimen to prevent or minimize the chance of the prediabetes from development into full diabetes, or to treat the prediabetes or diabetes.

The amino acid sequences of the prediabetes and diabetes protein markers are as follows: MLL4 (SEQ ID NO: 1); LAMA2 (SEQ ID NO: 2); PLXDC2 (SEQ ID NO: 3).

Abbreviations: BW, body weight; FBG, fasting blood glucose; IDF, International Diabetes Federation; IPA®, INGENUITY® pathway analysis; iTRAQ®, isobaric tags for relative and absolute quantitation; MS, Mass spectrometry; T2D, type 2 diabetes; TRIG, triglyceride; an ROC curve, an Receiver Operating Characteristic curve; AUC, Area under the ROC Curve.

The invention relates to identification and use of protein markers for diagnosis and treatment of prediabetes and diabetes.

A method for identifying prediabetes protein markers is disclosed, which comprises (a) collecting serum samples from non-prediabetic (healthy) and prediabetic subjects, respectively; (b) depleting high-abundance proteins in the serum samples; (c) digesting remaining proteins with trypsin to obtain digested protein fragments in the serum samples; (d) labeling each of the digested protein fragments with a different isobaric tags to obtain isobaric tag-labeled protein fragments for relative and absolute quantitation; (e) mixing the isobaric tag-labeled protein fragments in the serum samples; (f) fractionating the isobaric tag-labeled protein fragments in the serum samples by chromatography to collect fractions; (g) identifying low-abundance proteins in the fractions with LC-MS/MS and Mascot analyses; (h) selecting candidates for prediabetes protein markers by subjecting the identified low-abundance proteins to a volcano plot analysis; (i) grouping the selected candidates according to biological function; and (j) identifying the candidates with $p<0.01$ and average relative ratio >1.3 as prediabetes protein markers. The selecting step may select candidates exhibiting a fold change of greater than 1.3 with a p value of equal to or smaller than 0.05 in the volcano plot analysis. The abundant proteins may comprise albumin and IgG.

Three proteins Lama2, PLXDC2 and MLL4 were discovered as potential diagnostic biomarkers for prediabetes and diabetes. These protein markers Lama2, PLXDC2 and MLL4 have clinical applications for care and treatment of prediabetes and diabetes patients, including, but not limiting to, use of antibodies specific against Lama2, PLXDC2 and MLL4 in the manufacture of a diagnostic kit, a method of detecting and identifying prediabetes and/or diabetes, a diagnostic kit for detecting prediabetes and/or diabetes, and methods of using the diagnostic kit. The antibodies comprise capture and detection antibodies.

In the diagnostic kit device/apparatus, the levels of the capture and detection antibodies are optimized so that the test area only shows color signals when the levels of the markers are above a clinically significant threshold.

EXAMPLES

Methods

Chemicals and reagents. The chemicals/reagents used include acetonitrile (ACN), Tris 2-carboxyethyl phosphine (TCEP), methyl methanethiosulfonate (MMTS), triethylamonium bicarbonat (TEAB), trifluoroacetic acid (TFA), Potassium dihydrogen phosphate (KH2PO4) and potassium chloride (KCl).

Mice and human serum samples collection. Healthy humans and patients diagnosed with prediabetes were recruited at the Tri-Service General hospital for blood collection. Blood samples were collected from healthy volunteers and prediabetic patients under 12 hr fasting condition. The serum samples were separated from whole blood, aliquoted to avoid repeating freeze-and-thaw cycle and then stored at −80° C. Human body weight and height were measured for body mass index (BMI). The fasting blood glucose (FBG), hemoglobin A1c (HbA1c), triglyceride (TRIG), total cholesterol (TC), high-density lipoprotein cholesterol (HDL), low-density lipoprotein cholesterol (LDL), insulin and albumin were assayed by automated clinical laboratory methods. C57Bl/6J and C57Bl/6J obese (db/db) mice were obtained from the National Laboratory Animal Center (Taipei, Taiwan) and the Jackson Laboratory (Bar Harbor, ME, USA), respectively. At 4 and 6 weeks of age, body weights, FBG, HbA1c, TRIG, TC, HDL, LDL, insulin and albumin level were measured as previously mentioned (n=3/each group). Blood samples were obtained from the mice which had fasted 16 hr. The serum were separated from whole blood by centrifugation and stored at −80° C. The mice were housed and fed standard mouse chow and water in a specific pathogen-free animal room with controlled temperature (22±2° C.), humidity (55±10%) and light/dark cycle (12 hr/12 hr). All the animals were cared and used base on the protocol of the Institutional Animal Care and Use Committee.

Protein depletion. To augment the detection and identification of low-abundance proteins, the PROTEOPREP® immunoaffinity Albumin and IgG Depletion Kit from SIGMA-ALDRICH® was used to evaluate the efficiency of high abundance protein depletion from serum samples using the manufacture's protocol. The protein concentration was calculated using the BCA protein assay kit from THERMO FISHER SCIENTIFIC®.

Protein digestion and iTRAQ® labeling. An equal amount of total protein (100 ug) per depleted sample was diluted with 0.5M TEAB, reduced with 5 mM TCEP at 60° C. for 1 hr, alkylated using 10 mM MMTS at room temperature for 10 min and then digested with 10 μg trypsin at 37° C. for 16 hr. Subsequently, each sample from mice and humans was labeled with different iTRAQ® tag as follows: iTRAQ®—114 for 3 pooled healthy mice and humans, iTRAQ®—115, 116, 117 for 3 prediabetic mice and humans, respectively. The four samples from mice and humans were combined respectively, dried by speedvac, dissolved in 200 ul 5% ACN in 0.5% TFA and then desalted using C18 spin column. After drying by speedvac again, each sample was dissolved in 400 μl of 25% ACN/0.1 FA.

Strong cation exchange chromatography (SCX) fractionation. The iTRAQ® labeled samples were fractionated separately via strong cation exchange chromatography using polysulfoethyl A column (2.1×200 mm, Sum particle size, 300 Å pore size with the flow rate of 0.3 ml/min. The mobile phase (A) is 10 mM $KH_2PO_4$ in 25% ACN, pH 3.0 and (B) is 1M KCL and 10 mM $KH_2PO_4$ in 25% ACN, pH 3.0. The gradient of fractionation is showed below: 0% B for 5 min, 0-20% B for 55 min, 20%-60% for 10 min, 60% for 10 min and 60-0% B for 20 min. Fractions were dried by speedvac.

LC-MS/MS analysis. The dried fractions were dissolved in 200 ul of 5% ACN/0.5% TFA, desalted using C18 spin column, dried by speedvac again and dissolved with 40 μl of 5% ACN/0.1% FA for LC-MS/MS analysis. Q EXACTIVE™ mass spectrometer (THERMO FISHER SCIENTIFIC®, Waltham, MA, USA) coupled with HCD fragmentation mode was used to generate MS and MS/MS spectra. ULTIMATE™ 3000 RSLC system (THERMO FISHER SCIENTIFIC®) equipped with a C18 column (ACCLAIM™ PEPMAP™ RSLC, 75 um×150 mm, 2 μm, 100 Å) was used for LC separation with the flow rate of 0.25 ul/min and the mobile phase (A) 0.1% FA and (B) 95% ACN/0.1% FA. The gradient of analysis is showed below: 1% B for 5 min, 1-25% B for 25 min, 25%-60% for 15 min, 60-80% for 5 min, 80% B for 10 min, 80-99% for 5 min and 99% for 5 min.

iTRAQ® data analysis. Relative protein ratio and peptide identification were processed by Proteom Discover 1.4 for Mascot database search. All tandem mass spectra were searched for species of *Mus musculus* and *Homo sapiens* against the International Protein index database.

Protein signaling pathways and functional analysis. Functions and signaling pathway of serum proteins with differential expression between the health and prediabetic mice and humans were analyzed by INGENUITY® Pathway Analysis (IPA®) and PUBMED®.

Immunoblotting. Serum samples were collected from C57BL/6 (B6), non-diabetic (ND) and prediabetic (PD) db/db mice and then lysed by RIPA lysis buffer. Total protein (50 ug) of each organ/tissue from control and prediabetic mice was resolved by 6% and 10% sodium dodecyl sulfate polyacrylamide gel electrophoresis (SDS-PAGE), transferred onto nitrocellulose membrane, immunoblotted with the antibodies against LAMA2 (1:2500, LifeSpan BioSciences, Seattle, WA, USA), MLL4 (1:500, Santa Cruz, Dallas, TX, USA), PLXDC2 (1:1000, Novus Biologicals, Littleton, Colorado, USA) and horseradish peroxidase (HRP)-conjugated goat and rabbit anti-mouse IgG as secondary antibody. The membranes were detected using FLUORCHEM™ HD2 system (BIO-TECHNE™, Minneapolis, MN, USA) after developing with enhanced chemiluminescence (ECL) substrate (EMD Millipore, Billerica, MA, USA).

ROC curve The true positive rate (sensitivity) is plotted in function of the false positive rate (100-specificity) for different cut-off points of a parameter in a ROC curve. Each point on the ROC curve represents a sensitivity/specificity pair corresponding to a particular decision threshold. The area under the ROC curve (AUC) of MLL4, LAMA2 and PLXDC2 is a measure of how well a parameter can distinguish between two diagnostic groups (diseased/normal).

Statistical analysis. The data are presented as mean±standard error of the mean (SEM). Student's t-test was used to compare the difference between two groups unless indicated otherwise. Comparisons between multiple groups were made with ANOVA. P values less than 0.05 were considered statistically significant.

Results

Comparison of the differentially expressed proteins in healthy and prediabetic sera of mouse and human origins using a quantitative proteomic approach. To characterize novel and reliable markers for (pre)diabetes, a combination of iTRAQ® and MS techniques was used to analyze the sera of non-prediabetic (healthy) and prediabetic db/db mice and humans (FIG. 1). Table 1 shows mouse body weight (BW) and serum biochemistry characteristics.

TABLE 1

| Clinical characteristics | Healthy (n = 3) | Pre-diabetic (n = 3) |
|---|---|---|
| Age (week) | 4.0 ± 0.0 | 6.0 ± 0.0 |
| Body weight (g) | 16.1 ± 0.4 | 30.7*** ± 0.7 |
| FBG (mg/dL) | 80.0 ± 2.5 | 117.3 *** ± 2.0 |
| HbA1c (%) | 3.7 ± 0.3 | 6.7 *** ± 0.0 |
| TRIG (mg/dL) | 79.3 ± 4.3 | 118.3*** ± 0.3 |
| TC (mg/dL) | 119.0 ± 0.7 | 116.0 ± 5.5 |
| HDL (mg/dL) | 100.7 ± 0.7 | 104.7 ± 4.8 |
| LDL (mg/dL) | 15.9 ± 0.2 | 18.0*** ± 0.0 |
| Fasting insulin (ng/ml) | 3.2 ± 0.0 | 6.0*** ± 0.1 |
| Albumin (g/dL) | 3.1 ± 0.1 | 3.9 ± 0.3 |

The parameters of the groups ate indicated as mean ± standard error. The parameters with significant change (P ≤ 0.05) between the healthy and pre-diabetic mice are indicated with asterisk(s).

Healthy and prediabetic mice were grouped based on their fasting blood glucose (FBG). We found that BW, FBG, HbA1c, triglyceride (TRIG) and fasting insulin were significantly different between both groups (Table 1.). Serum samples from both groups were collected and their abundant proteins were then depleted, followed by trypsin digestion individually. Three health mouse sera were pooled together to minimize individual variability and then labeled with iTRAQ® 114. Three prediabetic mouse sera were labeled with iTRAQ® 115, 116 and 117, respectively. Finally, four iTRAQ® samples were mixed up and analyzed by LC-MS/MS (FIG. 1). The identity of the serum proteins from healthy and prediabetic mice was confirmed using Mascot software (FIG. 1). We identified total 442 serum proteins from mice at the peptide score of ≥20, the peptide matches ≥2 and the unique peptide matches ≥1.

We followed the same approach to characterize the serum proteins of healthy and prediabetic subjects to compare and validate the markers between men and mice (Discovery, FIG. 1). The body mass index (BMI) and serum biochemistry of human subjects were analyzed (Table 2). We found that age, FBG, HbA1c, fasting insulin and albumin are significantly different (P<0.05) between healthy and prediabetic groups (Table 2). Serum samples from men were collected. After abundant proteins were depleted, the remaining proteins were digested with trypsin. The sera of 3 healthy volunteers were pooled and labeled with iTRAQ® 114. The sera of 3 prediabetic ones were labeled with iTRAQ® 115, 116 and 117, respectively. A pool of four iTRAQ® samples were analyzed by LC-MS/MS and their identity was ascertained using the Mascot analysis (FIG. 1). Total 500 proteins were identified in the sera of both groups at the peptide score ≥20, the peptide matches ≥2 and the unique peptide matches ≥1 (Table 3). Table 2 shows characteristics of humans.

TABLE 2

| Clinical characteristics | Healthy (n = 3) | Pre-diabetic (n = 3) |
|---|---|---|
| Age (year) | 26.7 ± 0.9 | 60.7** ± 5.8 |
| BMI | 23.9 ± 2.9 | 23.4 ± 1.3 |
| FBG (mg/dL) | 86.7 ± 0.9 | 112.0** ± 3.2 |
| HbA1c (%) | 5.3 ± 0.2 | 6.5* ± 0.2 |
| TRIG (mg/dL) | 79.0 ± 10.4 | 102.0 ± 18.6 |
| TC (mg/dL) | 169.3 ± 20.2 | 161.3 ± 2.8 |
| HDL (mg/dL) | 57.5 ± 7.4 | 50.0 ± 5.9 |
| LDL (mg/dL) | 79.0 ± 11 | 91.3 ± 8.4 |
| Fasting insulin (μU/L) | 3.5 ± 0.1 | 10.5* ± 1.6 |
| Albumin (g/dL) | 5.2 ± 0.2 | 4.4* ± 0.1 |

The parameters of the groups are indicated as mean ± standard error. The parameters with significant change (P ≤ 0.05) between the healthy and pre-diabetic subjects are indicated with asterisk(s).

TABLE 3

| SN | Accession No. | ID[#] | [a]ARPR | log 10 (P value) | Functional categorization[##] | Cellular components* | Molecular function** |
|---|---|---|---|---|---|---|---|
| 1 | IPI00020019 | ADIPOQ | 3.771 | 1.74 | DB | ECS | OT |
| 2 | IPI00218725 | LAMA2 | 2.707 | 2.27 | DB | ECS | OT |
| 3 | IPI00296534 | FBLN1 | 2.382 | 1.87 | DBCC | ECS | OT |
| 4 | IPI00304273 | APOA4 | 2.233 | 1.94 | OB | ECS | TP |
| 5 | IPI00385555 | IGKV | 2.121 | 1.70 | IM | UM | UM |
| 6 | IPI00216065 | PROZ | 2.089 | 1.30 | CL | ECS | PD |
| 7 | IPI00550363 | TAGLN2 | 1.998 | 1.86 | OB | CP | OT |
| 8 | IPI00909594 | C7 | 1.929 | 1.81 | IM | ECS | OT |
| 9 | IPI00829845 | IGHV | 1.902 | 1.44 | IM | UM | UM |
| 10 | IPI00296608 | C7 Complement | 1.861 | 1.86 | IM | ECS | OT |
| 11 | IPI00941345 | TNXB | 1.859 | 1.71 | DBCC | ECS | OT |
| 12 | IPI00171678 | DBH | 1.849 | 1.31 | DB | CP | ENZ |
| 13 | IPI00064667 | CNDP1 | 1.834 | 1.40 | DBCC | CP | PD |
| 14 | IPI00975939 | SAA2-SAA4 | 1.824 | 2.04 | DB | OT | TP |
| 15 | IPI00007240 | F13B | 1.756 | 1.38 | CL | ECS | ENZ |
| 16 | IPI00044369 | PLXDC2 | 1.741 | 2.16 | DBCC | ECS | OT |
| 17 | IPI00239405 | SYNE2 | 1.683 | 1.88 | DB | NCL | OT |
| 18 | IPI00006662 | APOD | 1.644 | 1.47 | OB | ECS | TP |
| 19 | IPI00291175 | VCL | 1.634 | 1.95 | DB | CP | ENZ |
| 20 | IPI00005809 | SDPR | 1.595 | 1.32 | OB | CP | OT |
| 21 | IPI00478003 | A2M | 1.554 | 1.33 | DB | ECS | TP |
| 22 | IPI00879709 | C6 Complement | 1.491 | 1.70 | IM | ECS | OT |
| 23 | IPI00029260 | CD14 | 1.491 | 2.51 | OB | CP | TMR |
| 24 | IPI00025426 | PZP | 1.490 | 1.31 | DB | ECS | OT |
| 25 | IPI00016334 | MCAM | 1.472 | 1.79 | DBCC | CP | OT |
| 26 | IPI00007199 | SERPINA10 | 1.449 | 1.31 | CL | ECS | OT |
| 27 | IPI00029193 | HGFAC | 1.446 | 1.40 | DB | ECS | PD |
| 28 | IPI00221224 | ANPEP | 1.431 | 1.93 | DBCC | PM | PD |
| 29 | IPI00026199 | GPX3 | 1.387 | 1.69 | DB | ECS | ENZ |
| 30 | IPI00451624 | CRTAC1 | 1.387 | 1.50 | OT, UNK | ECS | OT |
| 31 | IPI00011252 | C8A Complement | 1.375 | 1.36 | IM | ECS | OT |
| 32 | IPI00253036 | CD99 | 1.364 | 2.64 | DB | PM | OT |
| 33 | IPI00027827 | SOD3 | 1.361 | 1.61 | DB | ECS | ENZ |
| 34 | IPI00218823 | MLL4 | 1.360 | 2.76 | DB | NCL | TR |
| 35 | IPI00021842 | APOE | 1.348 | 1.88 | OB | ECS | TP |
| 36 | IPI00028030 | COMP | 1.330 | 1.51 | DBCC | ECS | OT |
| 37 | IPI00008494 | ICAM1 | 1.329 | 1.66 | DB | PM | TMR |
| 38 | IPI00166729 | AZGP1 | 1.326 | 1.46 | DB | ECS | TP |
| 39 | IPI00017603 | F8 | 1.312 | 1.37 | CL | ECS | PD |
| 40 | IPI00784869 | DNAH10 | 1.305 | 1.59 | OB | Other | OT |
| 41 | IPI00291262 | CLU | 1.304 | 2.42 | DB | CP | OT |
| 42 | IPI00795454 | CCDC57 Protein | 1.287 | 1.85 | OT, UNK | OT | OT |
| 43 | IPI00019580 | PLG | 1.274 | 2.02 | CL | ECS | PD |
| 44 | IPI00022937 | F5 | 1.238 | 1.35 | OT, UNK | PM | ENZ |
| 45 | IPI00298828 | APOH | 1.238 | 1.89 | CL | ECS | TP |
| 46 | IPI00746623 | HABP2 | 1.231 | 1.90 | CL | ECS | PD |

TABLE 3-continued

| SN | Accession No. | ID[#] | [a]ARPR | log 10 (P value) | Functional categorization[##] | Cellular components* | Molecular function** |
|---|---|---|---|---|---|---|---|
| 47 | IPI00983154 | VDAC3 Uncharacterized protein | 1.221 | 1.56 | DB | CP | IC |
| 48 | IPI00019576 | F10 | 1.219 | 1.53 | CL | ECS | PD |
| 49 | IPI00220986 | ADAMTS9 | 1.211 | 1.75 | CL | ECS | PD |
| 50 | IPI00296176 | F9 | 1.210 | 1.84 | CL | ECS | PD |
| 51 | IPI00027482 | SERPINA6 | 1.207 | 1.32 | OT, UNK | ECS | OT |
| 52 | IPI00292946 | SERPINA7 | 1.166 | 1.88 | OT, UNK | ECS | TP |
| 53 | IPI00004373 | MBL2 | 1.141 | 1.40 | DB | ECS | OT |
| 54 | IPI00019359 | KRT9 | 1.111 | 1.89 | OT, UNK | CP | OT |
| 55 | IPI00022432 | TTR | 1.081 | 1.56 | DB | ECS | TP |
| 56 | IPI00736763 | SERPINA2 | 1.073 | 2.96 | OT, UNK | ECS | OT |
| 57 | IPI00026944 | NID1 | 1.070 | 2.19 | OT, UNK | ECS | OT |
| 58 | IPI00385985 | IGLV | 0.854 | 1.56 | IM | UM | UM |
| 59 | IPI00218795 | SELL | 0.777 | 1.53 | IM | PM | TMR |
| 60 | IPI00384409 | IGHV | 0.715 | 1.39 | IM | UM | UM |
| 61 | IPI00829701 | 13 kDa protein | 0.704 | 1.61 | OT, UNK | UM | UM |
| 62 | IPI00009792 | IGHV1OR15-1 | 0.700 | 1.61 | IM | OT | OT |
| 63 | IPI00827724 | IGHV3-7 | 0.696 | 1.64 | IM | OT | OT |
| 64 | IPI00854589 | Conserved hypothetical protein | 0.696 | 1.62 | OT, UNK | OT | OT |
| 65 | IPI00382682 | Putative matrix cell adhesion molecule-3 | 0.696 | 1.63 | OT, UNK | UM | UM |
| 66 | IPI00382678 | Putative uncharacterized protein | 0.690 | 1.65 | OT, UNK | OT | OT |
| 67 | IPI00027547 | DCD | 0.681 | 1.60 | OT, UNK | ECS | OT |
| 68 | IPI00022445 | PPBP | 0.657 | 1.40 | CL | ECS | CK |
| 69 | IPI00973474 | IGHG3 | 0.649 | 1.33 | IM | ECS | OT |
| 70 | IPI00021364 | CFP | 0.580 | 1.74 | IM | ECS | OT |

[a]The ARPR represents average relative protein ratio as a ratio of protein expression in pre-diabetic patients as compared to healthy volunteers. Up- and down -regulated proteins are indicated in red and green colors respectively.

[#](1) ADIPOQ, Adiponectin; (2) LAMA2, Laminin subunit alpha-2 isoform b precursor; (3) FBLN1, Isoform D of Fibulin-1; (4) APOA4, Apolipoprotein A-IV; (5) IGKV, Ig kappa chain V-I region BAN; (6) PROZ; Isoform 2 of Vitamin K-dependent protein Z; (7) TAGLN2, Transgelin-2; (8) C7, cDNA FLJ58413, highly similar to Complement component C7; (9) IGHV, Immunoglobulin heavy chain variable region; (10) C7 Complement, Component C7; (11) TNXB, Tenascin XB; (12) DBH, Dopamine beta-hydroxylase; (13) CNDP1, Beta-Ala-His dipeptidase; carnosinase; (14) SAA2-SAA4, SAA2-SAA2 protein; (15) F13B, Coagulation factor XIII B chain; (16) PLXDC2, Isoform 1 of Plexin domain-containing protein 2; (17) SYNE2, Isoform 1 of Nesprin-2; (18) APOD, Apolipoprotein D; (19) VCL, Isoform 1 of Vinculin; (20) SDPR, Serum deprivation-response protein; cavin 2; (21) A2M, Alpha-2-macroglobulin; (22) C6 Complement, Component C6 precursor; (23) CD14, Monocyte differentiation antigen CD14; (24) PZP, Isoform 1 of Pregnancy zone protein; (25) MCAM, Isoform 1 of Cell surface glycoprotein MUC18 = CD146; (26) SERPINA10, Protein Z-dependent protease inhibitor; (27) HGFAC, Hepatocyte growth factor activator; (28) ANPEP, Aminopeptidase N; (29) GPX3, Glutathione peroxidase 3; (30) CRTAC1, Isoform 1 of Cartilage acidic protein 1; (31) C8A Complement, Component C8 alpha chain; (32) CD99, Isoform 1 of CD99 antigen; (33) SOD3, Extracellular superoxide dismutase [Cu—Zn]; (34) MLL4, Isoform 1 of Histone-lysine N-methyltransferase MLL4 (ASC2 complex); (35) APOE, Apolipoprotein E; (36) COMP, Cartilage oligomeric matrix protein; (37) ICAM1, Intercellular adhesion molecule 1; (38) AZGP1, Zinc-alpha-2-glycoprotein; (39) F8, Coagulation factor VIII; (40) DNAH10, Isoform 1 of Dynein heavy chain 10, axonemal; (41) CLU, Isoform 1 of Clusterin; (42) CCDC57 Protein, Coiled-coil domain containing 57; (43) PEG, Plasminogen; (44) F5, 252 kDa protein; (45) APOH, Beta-2-glycoprotein 1; (46) HABP2, Hyaluronan-binding protein 2; (47) VDAC3 Uncharacterized protein, Voltage-dependent anion channel 3 uncharacterized protein; (48) (F10, Coagulation factor X; (49) ADAMTS9, Isoform 3 of A disintegrin and metalloproteinase with thrombospondin motifs 9; (50) F9, Coagulation factor IX; (51) SERPINA6, Corticosteroid-binding globulin; (52) SERPINA7, Thyroxine-binding globulin; (53) MBL2, Mannose-binding protein C; (54) KRT9, Keratin, type I cytoskeletal 9; (55) TTR, Transthyretin; (56) SERPINA2, Putative alpha-1-antitrypsin-related protein; (57) NID1, Isoform 1 of Nidogen-1; (58) IGLV, Ig lambda chain V-III region; (59) SELL, L-selectin precursor; (60) IGHV, Myosin-reactive immunoglobulin heavy chain variable region; (61) IGHV1OR15-1, Ig heavy chain V-I region V35; (62) IGHV3-7, Rheumatoid factor Vh I region; (63) DCD, Dermcidin; (64) PPBP, Platelet basic protein; (65) IGHG3, Putative uncharacterized protein; (66) CFP, Properdin.

[##]CL, Coagulation; DB, Diabetes; OB, Obesity; DBCC, Diabetic complications; IM, Immunity; Others, unknown (OT, UNK).

*ECS, Extracellular Space; CP, Cytoplasm; Unmapped (UM); Other (OT); Nucleus (NCL); Plasma Membrane (PM).

**CK, Cytokine; ENZ, Enzyme; IC, ion channel; OT, Other; PD, Peptidase; TMR, transmembrane receptor; TR, transcription regulator; TP, Transporter; UM, Unmapped.

Gene Ontology and Pathway Analysis of the Selected Serum Proteins.

To gain insightful information about the biological function of the selected 70 proteins as shown in Table 3, these proteins were analyzed by gene ontology and PUBMED® references searching (FIGS. 5A-5C). Those proteins can be classified into 6 functional categories related to diabetes, diabetic complications, obesity, inflammatory immunity, coagulation and others (FIG. 5A).

Next, we narrowed down the number of candidate markers by picking up those proteins with P<0.01 and average relative ratio >1.3. Seven proteins, laminin subunit alpha 2 (LAMA2), serum amyloid A 2 (SAA2), plexin domain containing 2 (PLXDC2), monocyte differentiation antigen CD14 (CD14), CD99 antigen (CD99), histone-lysine N-methyltransferase MLL4 (MLL4), and clusterin (CLLU), stood out under this stringent selection conditions. This screening strategy for the identification of potential markers for (pre)diabetes worked well. For example, CD99 (EP1828774 A1) and CLU (U.S. Pat. No. 8,673,644 B2) were patented as diabetic markers. SAA was reported to be increased in plasma of obese and insulin resistant humans and was a marker of insulin resistance in mice. CD14 was reported to modulate inflammation-driven insulin resistance and was identified as an inflammatory marker in women with diabetes and impaired glucose tolerance. These 4 proteins showed that our data are highly reliable. Furthermore, several lines of evidences showed that the rest of 3 proteins are novel markers for diabetes. MLL4 was reported to interact with the transcription factors to regulate islet β-cell function. LAMA2 mutation was shown to cause merosin-deficient congenital muscular dystrophy. PLXDC2 was known to regulate differentiation and proliferation during the development of nervous system.

To better understand the biological meaning of the changes in these proteins before and during T2D, the web-based IPA® and PUBMED® database searching were used to predict protein signaling pathways (FIG. 3). IPA® generated the network of a total of 35 proteins related to connective tissue disorders, dermatological diseases and conditions, and developmental disorders. The putative signaling pathways need to be ascertained with further experiments.

Confirmation of MLL4, LAMA2 and PLXDC2 for Potential Markers by Immunoblotting.

Figure 4:
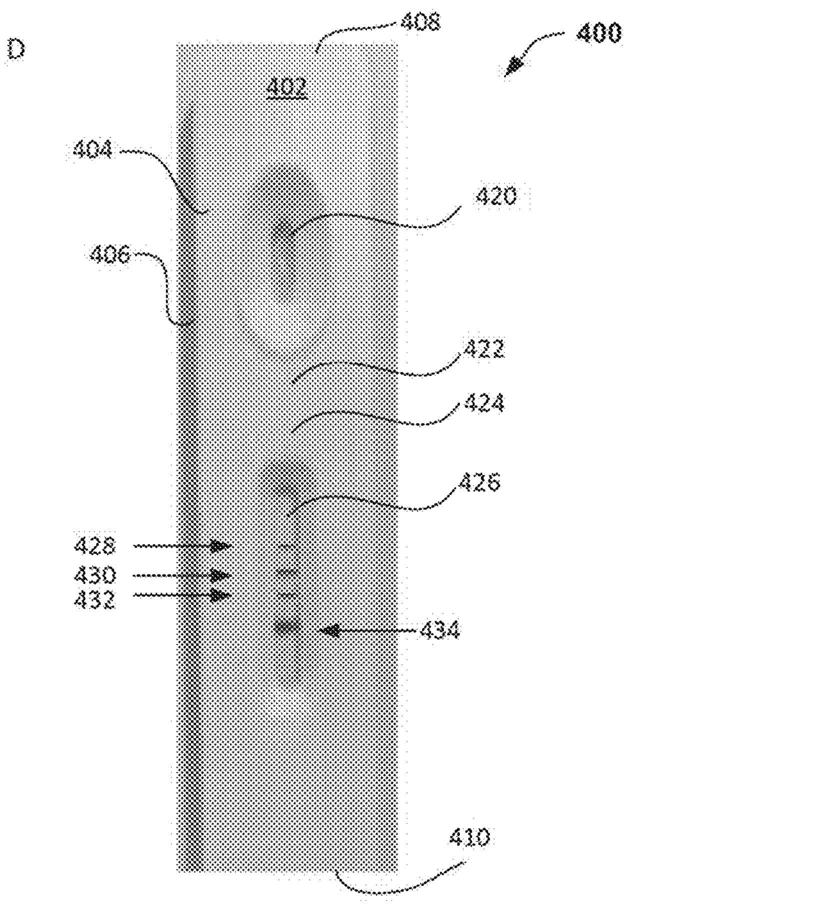
FIG. 4 shows results of immunoblotting analysis, diagnostic efficacy and diagnostic values of LAMA2, PLXDC2 and MLL4 in healthy and (pre)diabetic sera of human origin. A. Serum samples from healthy and (pre)diabetic subjects were collected and then lysed with lysis buffer. After centrifugation, total lysates were prepared for immunoblotting analysis with antibodies as indicated. B. Diagnosis efficacy was analyzed using ROC curve. C. Sensitivity, specificity and accuracy were evaluated for diagnostic value. D. An image of a diagnostic kit apparatus useful for detecting (pre)diabetes using multiple protein markers.

To verify the feasibility of using the 7 serum proteins MLL4, LAMA2, PLXDC2, CD99, CLU, SAA2 and CD14 as prediabetic markers, MLL4, LAMA2 and PLXDC2 were selected due to their high statistical confidence and novelty. The published markers, CD99, CLU, SAA2 and CD14, were used to compare with novel markers for reliability. We confirmed the data with immunoblotting. The immunoblotting data pointed out that the serum level of MLL4, LAMA2 and PLXDC2 was up-regulated in 5 prediabetic subjects (FIG. 4A). The ROC curve was used as a tool for diagnostic test evaluation. The ROC diagram was used to illustrate the diagnostic efficacy of the serum MLL4, LAMA2 and PLXDC2. Their discrimination thresholds and the area under the curve (AUC) was used to evaluate the diagnostic value of each protein. The AUC of MLL4, LAMA2 and PLXDC2 were 0.95795, 0.9257 and 0.91445, respectively (FIG. 4B). The sensitivity, specificity and accuracy of MLL4, LAMA2 and PLXDC2 were all 71.42%, 71.42% and 71.42%, respectively (FIG. 4C).

FIG. 4D illustrates a diagnostic kit device/apparatus ("diagnostic kit") 400 for detecting prediabetes and/or diabetes using multiple protein markers. The diagnostic kit 400 comprises the following: (i) a substrate 402 having a top surface 404 and a bottom surface 406 opposite to the top surface 404, and a top end 408 and a bottom end 410 opposite to the top end 408; (ii) a sample loading area 420; (iii) a capture antibody area (a test reading area) 426, containing capture antibodies to capture prediabetes and diabetes protein markers comprising MLL4 428, LAMA2 430, and PLXDC2 432; (iv) a reagent area 424, being coated with a conditioning reagent; (v) a detection antibody area 422, containing detection antibodies to visualize the captured prediabetes and diabetes protein markers comprising the MLL4 428, LAMA2 430, and PLXDC2 432 in the captured antibody area (test reading area) 426; and (vi) optionally a positive control area 434, wherein the sample loading area 420, the detection antibody area 422, the reagent area 424, the capture antibody area 426, and the positive control area 434 are located on the top surface 404 of the substrate 402, allowing these areas to be in fluidic communication, the sample loading area 420 being located at the top end 408 and the capture antibody area 426 located at the bottom end 410 with the optionally positive control area 434 located either after or before the capture antibody area 426.

Other prediabetes and diabetes protein markers may also be included together with the MLL4 428, LAMA2 430, and PLXDC2 432 in the diagnostic kit device/apparatus 400 of the invention. Under this situation, the capture antibodies further comprise antibodies specific against other prediabetes and diabetes protein markers. The sample loading area 420, the detection antibody area 422, the reagent area 424, and the capture antibody area 426 may be sequentially located on the top surface 404 of the substrate 402 with the optionally positive control area 434 being located either after or before the capture antibody area 426. Alternatively, the sample loading area 420, the reagent area 424, the detection antibody area 422, and the capture antibody area 426 are sequentially located with the optionally positive control area 434 being located either after or before the capture antibody area 426.

The capture antibody area 426 contains antibodies (primary antibodies) against the analytes (protein markers), which are immobilized to the area 426. The detection antibody area 422 contains antibodies (secondary antibodies) against the analytes (protein markers) which are conjugated to either an enzyme or other molecule to visualize the binding reaction in the capture antibody area (or test reading area) 426. Examples of the enzyme may be horseradish peroxidase (HRP) or alkaline phosphatase (AP). The reagent area may contain color-forming substrate(s) and buffer(s) when enzyme-based assay detection system is used, or only buffers when non-enzyme-based assay detection system is used. The positive control area serves to show that the diagnostic kit functions properly. It may contain an immobilized non-conjugated enzyme, or an immobilized antibody against one of more the detection antibodies. All the antibodies and reagents are either adsorbed, coated or immobilized onto the substrate.

The diagnostic kit device/apparatus of the invention was designed to perform lateral flow immunoassay such as disclosed by U.S. Pat. No. 8,399,261 and Serebrennikova et al. (2018) ("Hierarchical Nanogold Labels to Improve the Sensitivity of Lateral Flow Immunoassay" Nano-Micro Lett. 10:24), both of which are incorporated herein in their entireties by reference.

In summary, we used a combination of iTRAQ® and MS techniques to identify proteins in human and mouse sera and quantify their amounts. INGENUITY® pathway analysis (IPA®) was used to predict the likely interaction network and pathways of the selected proteins. The level of three serum proteins was further confirmed using immunoblotting analysis and the receiver operating characteristic (ROC) curve analysis. The data suggest that a combination of iTRAQ® and MS techniques is able to identify serum proteins as potential markers for (pre)diabetes. MLL4, LAMA2 and PLXDC2 could be suitable diagnostic markers for (pre)diabetes. Among these proteins, MLL4 is the most potential marker for diagnosis.

The embodiments and examples were chosen and described to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. All references cited and discussed in this specification are incorporated herein by reference in their entireties and to the same extent as if each reference was individually incorporated by reference.

What is claimed is:

1. A lateral flow diagnostic device for detecting and identifying prediabetes and/or diabetes, comprising:

(i) a substrate having a top surface and a bottom surface opposite to the top surface, and a top end and a bottom end opposite to the top end;

(ii) a sample loading area;

(iii) a capture antibody area, containing capture antibodies immobilized to the substrate in the capture antibody area to capture prediabetes and diabetes protein markers consisting of MLL4, LAMA2 and PLXDC2;

(iv) a reagent area, containing a conditioning reagent;

(v) a detection antibody area, containing detection antibodies to detect the captured prediabetes and diabetes protein markers consisting of the MLL4, LAMA2 and PLXDC2; and (vi) optionally a positive control area;

wherein the sample loading area, the detection antibody area, the reagent area, the capture antibody area, and the positive control area are located on the top surface of the substrate, allowing these areas to be in fluidic communication, the sample loading area being located at the top end and the capture antibody area located at the bottom end with the optionally positive control area located either after or before the capture antibody area.

2. The lateral flow diagnostic device of claim 1, wherein the capture antibodies and detection antibodies are polyclonal antibodies.

3. The lateral flow diagnostic device of claim 1, wherein the capture antibodies and detection antibodies are monoclonal antibodies.

4. The lateral flow diagnostic device of claim 1, wherein the detection antibodies are labeled with colloidal gold, or a color-generating enzyme, and the conditioning reagent comprises a substrate for the color-generating enzyme.

5. A method for detecting and identifying prediabetes and/or diabetes, comprising:

(a) providing the lateral flow diagnostic device of claim 1;

(b) supplying a serum sample from a subject in need thereof, and (c) detecting whether the levels of prediabetes and diabetes protein markers consisting of MLL4, LAMA2 and PLXDC2 in the serum sample are increased as compared with a healthy control, wherein an increase in the levels of the protein markers MLL4, LAMA2, and PLXDC2 is indicative of the subject in need thereof having the prediabetes or diabetes.

6. The method of claim 5, wherein the detection antibody area shows color signals when the levels of the markers in the serum sample are above a decision threshold.

7. The method of claim 5, wherein the detecting step is performed by visualizing a color change.

8. A method of manufacture of the lateral flow diagnostic device for detecting prediabetes and/or diabetes of claim 1, comprising providing a set of antibodies with specific binding affinities to prediabetes and diabetes protein markers consisting of MLL4, LAMA2, and PLXDC2, wherein the set of antibodies comprises:

(a) a first antibody having a specific binding affinity to the MLL4;

(b) a second antibody having a specific binding affinity to the LAMA2; and (c) a third antibody having a specific binding affinity to the PLXDC2.

* * * * *

SEQUENCE LISTING

<160> NUMBER OF SEQ ID NOS: 3

<210> SEQ ID NO 1
<211> LENGTH: 2715
<212> TYPE: PRT
<213> ORGANISM: Homo sapiens

<400> SEQUENCE: 1

Met Ala Ala Ala Ala Gly Gly Gly Ser Cys Pro Gly Pro Gly Ser Ala
1 5 10 15

Arg Gly Arg Phe Pro Gly Arg Pro Arg Gly Ala Gly Gly Gly Gly Gly
20 25 30

Arg Gly Gly Arg Gly Asn Gly Ala Glu Arg Val Arg Val Ala Leu Arg
35 40 45

Arg Gly Gly Gly Ala Thr Gly Pro Gly Gly Ala Glu Pro Gly Glu Asp
50 55 60

Thr Ala Leu Leu Arg Leu Leu Gly Leu Arg Arg Gly Leu Arg Arg Leu
65 70 75 80

Arg Arg Leu Trp Ala Gly Pro Arg Val Gln Arg Gly Arg Gly Arg Gly
85 90 95

Arg Gly Arg Gly Trp Gly Pro Ser Arg Gly Cys Val Pro Glu Glu Glu
100 105 110

Ser Ser Asp Gly Glu Ser Asp Glu Glu Glu Phe Gln Gly Phe His Ser
115 120 125

Asp Glu Asp Val Ala Pro Ser Ser Leu Arg Ser Ala Leu Arg Ser Gln
130 135 140

Arg Gly Arg Ala Pro Arg Gly Arg Gly Arg Lys His Lys Thr Thr Pro
145 150 155 160

Leu Pro Pro Pro Arg Leu Ala Asp Val Ala Pro Thr Pro Pro Lys Thr
165 170 175

Pro Ala Arg Lys Arg Gly Glu Glu Gly Thr Glu Arg Met Val Gln Ala
180 185 190

Leu Thr Glu Leu Leu Arg Arg Ala Gln Ala Pro Gln Ala Pro Arg Ser
195 200 205

Arg Ala Cys Glu Pro Ser Thr Pro Arg Arg Ser Arg Gly Arg Pro Pro
210 215 220

Gly Arg Pro Ala Gly Pro Cys Arg Arg Lys Gln Gln Ala Val Val Val
225 230 235 240

Ala Glu Ala Ala Val Thr Ile Pro Lys Pro Glu Pro Pro Pro Pro Val
245 250 255

Val Pro Val Lys His Gln Thr Gly Ser Trp Lys Cys Lys Glu Gly Pro
260 265 270

Gly Pro Gly Pro Gly Thr Pro Arg Arg Gly Gly Gln Ser Ser Arg Gly
275 280 285

Gly Arg Gly Gly Arg Gly Arg Gly Arg Gly Gly Gly Leu Pro Phe Val
290 295 300

Ile Lys Phe Val Ser Arg Ala Lys Lys Val Lys Met Gly Gln Leu Ser
305 310 315 320

Leu Gly Leu Glu Ser Gly Gln Gly Gln Gly Gln His Glu Glu Ser Trp
325 330 335

Gln Asp Val Pro Gln Arg Arg Val Gly Ser Gly Gln Gly Gly Ser Pro
340 345 350

Cys Trp Lys Lys Gln Glu Gln Lys Leu Asp Asp Glu Glu Glu Glu Lys
355 360 365

-continued

```
Lys Glu Glu Glu Glu Lys Asp Lys Glu Gly Glu Glu Lys Glu Glu Arg
    370                 375                 380

Ala Val Ala Glu Glu Met Met Pro Ala Ala Glu Lys Glu Glu Ala Lys
385                 390                 395                 400

Leu Pro Pro Pro Pro Leu Thr Pro Pro Ala Pro Ser Pro Pro Pro Pro
                405                 410                 415

Leu Pro Pro Pro Ser Thr Ser Pro Pro Pro Pro Leu Cys Pro Pro Pro
            420                 425                 430

Pro Pro Pro Val Ser Pro Pro Pro Leu Pro Ser Pro Pro Pro Pro Pro
        435                 440                 445

Ala Gln Glu Glu Gln Glu Glu Ser Pro Pro Pro Val Val Pro Ala Thr
    450                 455                 460

Cys Ser Arg Lys Arg Gly Arg Pro Pro Leu Thr Pro Ser Gln Arg Ala
465                 470                 475                 480

Glu Arg Glu Ala Ala Arg Ala Gly Pro Glu Gly Thr Ser Pro Pro Thr
                485                 490                 495

Pro Thr Pro Ser Thr Ala Thr Gly Gly Pro Pro Glu Asp Ser Pro Thr
            500                 505                 510

Val Ala Pro Lys Ser Thr Thr Phe Leu Lys Asn Ile Arg Gln Phe Ile
        515                 520                 525

Met Pro Val Val Ser Ala Arg Ser Ser Arg Val Ile Lys Thr Pro Arg
    530                 535                 540

Arg Phe Met Asp Glu Asp Pro Pro Lys Pro Pro Lys Val Glu Val Ser
545                 550                 555                 560

Pro Val Leu Arg Pro Pro Ile Thr Thr Ser Pro Pro Val Pro Gln Glu
                565                 570                 575

Pro Ala Pro Val Pro Ser Pro Pro Arg Ala Pro Thr Pro Pro Ser Thr
            580                 585                 590

Pro Val Pro Leu Pro Glu Lys Arg Arg Ser Ile Leu Arg Glu Pro Thr
        595                 600                 605

Phe Arg Trp Thr Ser Leu Thr Arg Glu Leu Pro Pro Pro Pro Pro Ala
    610                 615                 620

Pro Pro Pro Pro Pro Ala Pro Ser Pro Pro Pro Ala Pro Ala Thr Ser
625                 630                 635                 640

Ser Arg Arg Pro Leu Leu Leu Arg Ala Pro Gln Phe Thr Pro Ser Glu
                645                 650                 655

Ala His Leu Lys Ile Tyr Glu Ser Val Leu Thr Pro Pro Pro Leu Gly
            660                 665                 670

Ala Pro Glu Ala Pro Glu Pro Glu Pro Pro Pro Ala Asp Asp Ser Pro
        675                 680                 685

Ala Glu Pro Glu Pro Arg Ala Val Gly Arg Thr Asn His Leu Ser Leu
    690                 695                 700

Pro Arg Phe Ala Pro Val Val Thr Thr Pro Val Lys Ala Glu Val Ser
705                 710                 715                 720

Pro His Gly Ala Pro Ala Leu Ser Asn Gly Pro Gln Thr Gln Ala Gln
                725                 730                 735

Leu Leu Gln Pro Leu Gln Ala Leu Gln Thr Gln Leu Leu Pro Gln Ala
            740                 745                 750

Leu Pro Pro Pro Gln Pro Gln Leu Gln Pro Pro Pro Ser Pro Gln Gln
        755                 760                 765

Met Pro Pro Leu Glu Lys Ala Arg Ile Ala Gly Val Gly Ser Leu Pro
    770                 775                 780

Leu Ser Gly Val Glu Glu Lys Met Phe Ser Leu Leu Lys Arg Ala Lys
```

-continued

```
785                 790                 795                 800

Val Gln Leu Phe Lys Ile Asp Gln Gln Gln Gln Gln Lys Val Ala Ala
                805                 810                 815

Ser Met Pro Leu Ser Pro Gly Gly Gln Met Glu Glu Val Ala Gly Ala
            820                 825                 830

Val Lys Gln Ile Ser Asp Arg Gly Pro Val Arg Ser Glu Asp Glu Ser
        835                 840                 845

Val Glu Ala Lys Arg Glu Arg Pro Ser Gly Pro Glu Ser Pro Val Gln
    850                 855                 860

Gly Pro Arg Ile Lys His Val Cys Arg His Ala Ala Val Ala Leu Gly
865                 870                 875                 880

Gln Ala Arg Ala Met Val Pro Glu Asp Val Pro Arg Leu Ser Ala Leu
                885                 890                 895

Pro Leu Arg Asp Arg Gln Asp Leu Ala Thr Glu Asp Thr Ser Ser Ala
            900                 905                 910

Ser Glu Thr Glu Ser Val Pro Ser Arg Ser Arg Arg Gly Lys Val Glu
        915                 920                 925

Ala Ala Gly Pro Gly Gly Glu Ser Glu Pro Thr Gly Ser Gly Gly Thr
    930                 935                 940

Leu Ala His Thr Pro Arg Arg Ser Leu Pro Ser His His Gly Lys Lys
945                 950                 955                 960

Met Arg Met Ala Arg Cys Gly His Cys Arg Gly Cys Leu Arg Val Gln
                965                 970                 975

Asp Cys Gly Ser Cys Val Asn Cys Leu Asp Lys Pro Lys Phe Gly Gly
            980                 985                 990

Pro Asn Thr Lys Lys Gln Cys Cys  Val Tyr Arg Lys Cys  Asp Lys Ile
        995                 1000                1005

Glu Ala  Arg Lys Met Glu Arg  Leu Ala Lys Lys Gly  Arg Thr Ile
    1010                1015                1020

Val Lys  Thr Leu Leu Pro Trp  Asp Ser Asp Glu Ser  Pro Glu Ala
    1025                1030                1035

Ser Pro  Gly Pro Pro Gly Pro  Arg Arg Gly Ala Gly  Ala Gly Gly
    1040                1045                1050

Pro Arg  Glu Glu Val Val Ala  His Pro Gly Pro Glu  Glu Gln Asp
    1055                1060                1065

Ser Leu  Leu Gln Arg Lys Ser  Ala Arg Arg Cys Val  Lys Gln Arg
    1070                1075                1080

Pro Ser  Tyr Asp Ile Phe Glu  Asp Ser Asp Asp Ser  Glu Pro Gly
    1085                1090                1095

Gly Pro  Pro Ala Pro Arg Arg  Arg Thr Pro Arg Glu  Asn Glu Leu
    1100                1105                1110

Pro Leu  Pro Glu Pro Glu Glu  Gln Ser Arg Pro Arg  Lys Pro Thr
    1115                1120                1125

Leu Gln  Pro Val Leu Gln Leu  Lys Ala Arg Arg Arg  Leu Asp Lys
    1130                1135                1140

Asp Ala  Leu Ala Pro Gly Pro  Phe Ala Ser Phe Pro  Asn Gly Trp
    1145                1150                1155

Thr Gly  Lys Gln Lys Ser Pro  Asp Gly Val His Arg  Val Arg Val
    1160                1165                1170

Asp Phe  Lys Glu Asp Cys Asp  Leu Glu Asn Val Trp  Leu Met Gly
    1175                1180                1185

Gly Leu  Ser Val Leu Thr Ser  Val Pro Gly Gly Pro  Pro Met Val
    1190                1195                1200
```

```
Cys Leu Leu Cys Ala Ser Lys Gly Leu His Glu Leu Val Phe Cys
    1205                1210                1215

Gln Val Cys Cys Asp Pro Phe His Pro Phe Cys Leu Glu Glu Ala
    1220                1225                1230

Glu Arg Pro Leu Pro Gln His His Asp Thr Trp Cys Cys Arg Arg
    1235                1240                1245

Cys Lys Phe Cys His Val Cys Gly Arg Lys Gly Arg Gly Ser Lys
    1250                1255                1260

His Leu Leu Glu Cys Glu Arg Cys Arg His Ala Tyr His Pro Ala
    1265                1270                1275

Cys Leu Gly Pro Ser Tyr Pro Thr Arg Ala Thr Arg Lys Arg Arg
    1280                1285                1290

His Trp Ile Cys Ser Ala Cys Val Arg Cys Lys Ser Cys Gly Ala
    1295                1300                1305

Thr Pro Gly Lys Asn Trp Asp Val Glu Trp Ser Gly Asp Tyr Ser
    1310                1315                1320

Leu Cys Pro Arg Cys Thr Gln Leu Tyr Glu Lys Gly Asn Tyr Cys
    1325                1330                1335

Pro Ile Cys Thr Arg Cys Tyr Glu Asp Asn Asp Tyr Glu Ser Lys
    1340                1345                1350

Met Met Gln Cys Ala Gln Cys Asp His Trp Val His Ala Lys Cys
    1355                1360                1365

Glu Gly Leu Ser Asp Glu Asp Tyr Glu Ile Leu Ser Gly Leu Pro
    1370                1375                1380

Asp Ser Val Leu Tyr Thr Cys Gly Pro Cys Ala Gly Ala Ala Gln
    1385                1390                1395

Pro Arg Trp Arg Glu Ala Leu Ser Gly Ala Leu Gln Gly Gly Leu
    1400                1405                1410

Arg Gln Val Leu Gln Gly Leu Leu Ser Ser Lys Val Val Gly Pro
    1415                1420                1425

Leu Leu Leu Cys Thr Gln Cys Gly Pro Asp Gly Lys Gln Leu His
    1430                1435                1440

Pro Gly Pro Cys Gly Leu Gln Ala Val Ser Gln Arg Phe Glu Asp
    1445                1450                1455

Gly His Tyr Lys Ser Val His Ser Phe Met Glu Asp Met Val Gly
    1460                1465                1470

Ile Leu Met Arg His Ser Glu Glu Gly Glu Thr Pro Asp Arg Arg
    1475                1480                1485

Ala Gly Gly Gln Met Lys Gly Leu Leu Leu Lys Leu Leu Glu Ser
    1490                1495                1500

Ala Phe Gly Trp Phe Asp Ala His Asp Pro Lys Tyr Trp Arg Arg
    1505                1510                1515

Ser Thr Arg Leu Pro Asn Gly Val Leu Pro Asn Ala Val Leu Pro
    1520                1525                1530

Pro Ser Leu Asp His Val Tyr Ala Gln Trp Arg Gln Gln Glu Pro
    1535                1540                1545

Glu Thr Pro Glu Ser Gly Gln Pro Pro Gly Asp Pro Ser Ala Ala
    1550                1555                1560

Phe Gln Gly Lys Asp Pro Ala Ala Phe Ser His Leu Glu Asp Pro
    1565                1570                1575

Arg Gln Cys Ala Leu Cys Leu Lys Tyr Gly Asp Ala Asp Ser Lys
    1580                1585                1590
```

```
Glu Ala  Gly Arg Leu Leu Tyr  Ile Gly Gln Asn Glu  Trp Thr His
    1595                 1600                 1605

Val Asn  Cys Ala Ile Trp Ser  Ala Glu Val Phe Glu  Glu Asn Asp
    1610                 1615                 1620

Gly Ser  Leu Lys Asn Val His  Ala Ala Val Ala Arg  Gly Arg Gln
    1625                 1630                 1635

Met Arg  Cys Glu Leu Cys Leu  Lys Pro Gly Ala Thr  Val Gly Cys
    1640                 1645                 1650

Cys Leu  Ser Ser Cys Leu Ser  Asn Phe His Phe Met  Cys Ala Arg
    1655                 1660                 1665

Ala Ser  Tyr Cys Ile Phe Gln  Asp Asp Lys Lys Val  Phe Cys Gln
    1670                 1675                 1680

Lys His  Thr Asp Leu Leu Asp  Gly Lys Glu Ile Val  Asn Pro Asp
    1685                 1690                 1695

Gly Phe  Asp Val Leu Arg Arg  Val Tyr Val Asp Phe  Glu Gly Ile
    1700                 1705                 1710

Asn Phe  Lys Arg Lys Phe Leu  Thr Gly Leu Glu Pro  Asp Ala Ile
    1715                 1720                 1725

Asn Val  Leu Ile Gly Ser Ile  Arg Ile Asp Ser Leu  Gly Thr Leu
    1730                 1735                 1740

Ser Asp  Leu Ser Asp Cys Glu  Gly Arg Leu Phe Pro  Ile Gly Tyr
    1745                 1750                 1755

Gln Cys  Ser Arg Leu Tyr Trp  Ser Thr Val Asp Ala  Arg Arg Arg
    1760                 1765                 1770

Cys Trp  Tyr Arg Cys Arg Ile  Leu Glu Tyr Arg Pro  Trp Gly Pro
    1775                 1780                 1785

Arg Glu  Glu Pro Ala His Leu  Glu Ala Ala Glu Glu  Asn Gln Thr
    1790                 1795                 1800

Ile Val  His Ser Pro Ala Pro  Ser Ser Glu Pro Pro  Gly Gly Glu
    1805                 1810                 1815

Asp Pro  Pro Leu Asp Thr Asp  Val Leu Val Pro Gly  Ala Pro Glu
    1820                 1825                 1830

Arg His  Ser Pro Ile Gln Asn  Leu Asp Pro Pro Leu  Arg Pro Asp
    1835                 1840                 1845

Ser Gly  Ser Ala Pro Pro Pro  Ala Pro Arg Ser Phe  Ser Gly Ala
    1850                 1855                 1860

Arg Ile  Lys Val Pro Asn Tyr  Ser Pro Ser Arg Arg  Pro Leu Gly
    1865                 1870                 1875

Gly Val  Ser Phe Gly Pro Leu  Pro Ser Pro Gly Ser  Pro Ser Ser
    1880                 1885                 1890

Leu Thr  His His Ile Pro Thr  Val Gly Asp Pro Asp  Phe Pro Ala
    1895                 1900                 1905

Pro Pro  Arg Arg Ser Arg Arg  Pro Ser Pro Leu Ala  Pro Arg Pro
    1910                 1915                 1920

Pro Pro  Ser Arg Trp Ala Ser  Pro Pro Leu Lys Thr  Ser Pro Gln
    1925                 1930                 1935

Leu Arg  Val Pro Pro Pro Thr  Ser Val Val Thr Ala  Leu Thr Pro
    1940                 1945                 1950

Thr Ser  Gly Glu Leu Ala Pro  Pro Gly Pro Ala Pro  Ser Pro Pro
    1955                 1960                 1965

Pro Pro  Glu Asp Leu Gly Pro  Asp Phe Glu Asp Met  Glu Val Val
    1970                 1975                 1980

Ser Gly  Leu Ser Ala Ala Asp  Leu Asp Phe Ala Ala  Ser Leu Leu
```

```
    1985                1990                1995

Gly Thr  Glu Pro Phe Gln Glu  Glu Ile Val Ala Ala  Gly Ala Met
    2000                2005                2010

Gly Ser  Ser His Gly Gly Pro  Gly Asp Ser Ser Glu  Glu Glu Ser
    2015                2020                2025

Ser Pro  Thr Ser Arg Tyr Ile  His Phe Pro Val Thr  Val Val Ser
    2030                2035                2040

Ala Pro  Gly Leu Ala Pro Ser  Ala Thr Pro Gly Ala  Pro Arg Ile
    2045                2050                2055

Glu Gln  Leu Asp Gly Val Asp  Asp Gly Thr Asp Ser  Glu Ala Glu
    2060                2065                2070

Ala Val  Gln Gln Pro Arg Gly  Gln Gly Thr Pro Pro  Ser Gly Pro
    2075                2080                2085

Gly Val  Val Arg Ala Gly Val  Leu Gly Ala Ala Gly  Asp Arg Ala
    2090                2095                2100

Arg Pro  Pro Glu Asp Leu Pro  Ser Glu Ile Val Asp  Phe Val Leu
    2105                2110                2115

Lys Asn  Leu Gly Gly Pro Gly  Asp Gly Gly Ala Gly  Pro Arg Glu
    2120                2125                2130

Glu Ser  Leu Pro Pro Ala Pro  Pro Leu Ala Asn Gly  Ser Gln Pro
    2135                2140                2145

Ser Gln  Gly Leu Thr Ala Ser  Pro Ala Asp Pro Thr  Arg Thr Phe
    2150                2155                2160

Ala Trp  Leu Pro Gly Ala Pro  Gly Val Arg Val Leu  Ser Leu Gly
    2165                2170                2175

Pro Ala  Pro Glu Pro Pro Lys  Pro Ala Thr Ser Lys  Ile Ile Leu
    2180                2185                2190

Val Asn  Lys Leu Gly Gln Val  Phe Val Lys Met Ala  Gly Glu Gly
    2195                2200                2205

Glu Pro  Val Pro Pro Pro Val  Lys Gln Pro Pro Leu  Pro Pro Thr
    2210                2215                2220

Ile Ser  Pro Thr Ala Pro Thr  Ser Trp Thr Leu Pro  Pro Gly Pro
    2225                2230                2235

Leu Leu  Gly Val Leu Pro Val  Val Gly Val Val Arg  Pro Ala Pro
    2240                2245                2250

Pro Pro  Pro Pro Pro Pro Leu  Thr Leu Val Leu Ser  Ser Gly Pro
    2255                2260                2265

Ala Ser  Pro Pro Arg Gln Ala  Ile Arg Val Lys Arg  Val Ser Thr
    2270                2275                2280

Phe Ser  Gly Arg Ser Pro Pro  Ala Pro Pro Pro Tyr  Lys Ala Pro
    2285                2290                2295

Arg Leu  Asp Glu Asp Gly Glu  Ala Ser Glu Asp Thr  Pro Gln Val
    2300                2305                2310

Pro Gly  Leu Gly Ser Gly Gly  Phe Ser Arg Val Arg  Met Lys Thr
    2315                2320                2325

Pro Thr  Val Arg Gly Val Leu  Asp Leu Asp Arg Pro  Gly Glu Pro
    2330                2335                2340

Ala Gly  Glu Glu Ser Pro Gly  Pro Leu Gln Glu Arg  Ser Pro Leu
    2345                2350                2355

Leu Pro  Leu Pro Glu Asp Gly  Pro Pro Gln Val Pro  Asp Gly Pro
    2360                2365                2370

Pro Asp  Leu Leu Leu Glu Ser  Gln Trp His His Tyr  Ser Gly Glu
    2375                2380                2385
```

```
Ala Ser  Ser Ser Glu Glu Glu  Pro Pro Ser Pro Asp  Asp Lys Glu
    2390                 2395                 2400

Asn Gln  Ala Pro Lys Arg Thr  Gly Pro His Leu Arg  Phe Glu Ile
    2405                 2410                 2415

Ser Ser  Glu Asp Gly Phe Ser  Val Glu Ala Glu Ser  Leu Glu Gly
    2420                 2425                 2430

Ala Trp  Arg Thr Leu Ile Glu  Lys Val Gln Glu Ala  Arg Gly His
    2435                 2440                 2445

Ala Arg  Leu Arg His Leu Ser  Phe Ser Gly Met Ser  Gly Ala Arg
    2450                 2455                 2460

Leu Leu  Gly Ile His His Asp  Ala Val Ile Phe Leu  Ala Glu Gln
    2465                 2470                 2475

Leu Pro  Gly Ala Gln Arg Cys  Gln His Tyr Lys Phe  Arg Tyr His
    2480                 2485                 2490

Gln Gln  Gly Glu Gly Gln Glu  Glu Pro Pro Leu Asn  Pro His Gly
    2495                 2500                 2505

Ala Ala  Arg Ala Glu Val Tyr  Leu Arg Lys Cys Thr  Phe Asp Met
    2510                 2515                 2520

Phe Asn  Phe Leu Ala Ser Gln  His Arg Val Leu Pro  Glu Gly Ala
    2525                 2530                 2535

Thr Cys  Asp Glu Glu Glu Asp  Glu Val Gln Leu Arg  Ser Thr Arg
    2540                 2545                 2550

Arg Ala  Thr Ser Leu Glu Leu  Pro Met Ala Met Arg  Phe Arg His
    2555                 2560                 2565

Leu Lys  Lys Thr Ser Lys Glu  Ala Val Gly Val Tyr  Arg Ser Ala
    2570                 2575                 2580

Ile His  Gly Arg Gly Leu Phe  Cys Lys Arg Asn Ile  Asp Ala Gly
    2585                 2590                 2595

Glu Met  Val Ile Glu Tyr Ser  Gly Ile Val Ile Arg  Ser Val Leu
    2600                 2605                 2610

Thr Asp  Lys Arg Glu Lys Phe  Tyr Asp Gly Lys Gly  Ile Gly Cys
    2615                 2620                 2625

Tyr Met  Phe Arg Met Asp Asp  Phe Asp Val Val Asp  Ala Thr Met
    2630                 2635                 2640

His Gly  Asn Ala Ala Arg Phe  Ile Asn His Ser Cys  Glu Pro Asn
    2645                 2650                 2655

Cys Phe  Ser Arg Val Ile His  Val Glu Gly Gln Lys  His Ile Val
    2660                 2665                 2670

Ile Phe  Ala Leu Arg Arg Ile  Leu Arg Gly Glu Glu  Leu Thr Tyr
    2675                 2680                 2685

Asp Tyr  Lys Phe Pro Ile Glu  Asp Ala Ser Asn Lys  Leu Pro Cys
    2690                 2695                 2700

Asn Cys  Gly Ala Lys Arg Cys  Arg Arg Phe Leu Asn
    2705                 2710                 2715


<210> SEQ ID NO 2
<211> LENGTH: 3122
<212> TYPE: PRT
<213> ORGANISM: Homo sapiens

<400> SEQUENCE: 2

Met Pro Gly Ala Ala Gly Val Leu Leu Leu Leu Leu Leu Ser Gly Gly
1               5                   10                  15

Leu Gly Gly Val Gln Ala Gln Arg Pro Gln Gln Gln Arg Gln Ser Gln
```

```
            20                  25                  30

Ala His Gln Gln Arg Gly Leu Phe Pro Ala Val Leu Asn Leu Ala Ser
        35                  40                  45

Asn Ala Leu Ile Thr Thr Asn Ala Thr Cys Gly Glu Lys Gly Pro Glu
    50                  55                  60

Met Tyr Cys Lys Leu Val Glu His Val Pro Gly Gln Pro Val Arg Asn
65                  70                  75                  80

Pro Gln Cys Arg Ile Cys Asn Gln Asn Ser Ser Asn Pro Asn Gln Arg
                85                  90                  95

His Pro Ile Thr Asn Ala Ile Asp Gly Lys Asn Thr Trp Trp Gln Ser
            100                 105                 110

Pro Ser Ile Lys Asn Gly Ile Glu Tyr His Tyr Val Thr Ile Thr Leu
        115                 120                 125

Asp Leu Gln Gln Val Phe Gln Ile Ala Tyr Val Ile Val Lys Ala Ala
    130                 135                 140

Asn Ser Pro Arg Pro Gly Asn Trp Ile Leu Glu Arg Ser Leu Asp Asp
145                 150                 155                 160

Val Glu Tyr Lys Pro Trp Gln Tyr His Ala Val Thr Asp Thr Glu Cys
                165                 170                 175

Leu Thr Leu Tyr Asn Ile Tyr Pro Arg Thr Gly Pro Pro Ser Tyr Ala
            180                 185                 190

Lys Asp Asp Glu Val Ile Cys Thr Ser Phe Tyr Ser Lys Ile His Pro
        195                 200                 205

Leu Glu Asn Gly Glu Ile His Ile Ser Leu Ile Asn Gly Arg Pro Ser
    210                 215                 220

Ala Asp Asp Pro Ser Pro Glu Leu Leu Glu Phe Thr Ser Ala Arg Tyr
225                 230                 235                 240

Ile Arg Leu Arg Phe Gln Arg Ile Arg Thr Leu Asn Ala Asp Leu Met
                245                 250                 255

Met Phe Ala His Lys Asp Pro Arg Glu Ile Asp Pro Ile Val Thr Arg
            260                 265                 270

Arg Tyr Tyr Tyr Ser Val Lys Asp Ile Ser Val Gly Gly Met Cys Ile
        275                 280                 285

Cys Tyr Gly His Ala Arg Ala Cys Pro Leu Asp Pro Ala Thr Asn Lys
    290                 295                 300

Ser Arg Cys Glu Cys Glu His Asn Thr Cys Gly Asp Ser Cys Asp Gln
305                 310                 315                 320

Cys Cys Pro Gly Phe His Gln Lys Pro Trp Arg Ala Gly Thr Phe Leu
                325                 330                 335

Thr Lys Thr Glu Cys Glu Ala Cys Asn Cys His Gly Lys Ala Glu Glu
            340                 345                 350

Cys Tyr Tyr Asp Glu Asn Val Ala Arg Arg Asn Leu Ser Leu Asn Ile
        355                 360                 365

Arg Gly Lys Tyr Ile Gly Gly Gly Val Cys Ile Asn Cys Thr Gln Asn
    370                 375                 380

Thr Ala Gly Ile Asn Cys Glu Thr Cys Thr Asp Gly Phe Phe Arg Pro
385                 390                 395                 400

Lys Gly Val Ser Pro Asn Tyr Pro Arg Pro Cys Gln Pro Cys His Cys
                405                 410                 415

Asp Pro Ile Gly Ser Leu Asn Glu Val Cys Val Lys Asp Glu Lys His
            420                 425                 430

Ala Arg Arg Gly Leu Ala Pro Gly Ser Cys His Cys Lys Thr Gly Phe
        435                 440                 445
```

```
Gly Gly Val Ser Cys Asp Arg Cys Ala Arg Gly Tyr Thr Gly Tyr Pro
    450                 455                 460

Asp Cys Lys Ala Cys Asn Cys Ser Gly Leu Gly Ser Lys Asn Glu Asp
465                 470                 475                 480

Pro Cys Phe Gly Pro Cys Ile Cys Lys Glu Asn Val Glu Gly Gly Asp
                485                 490                 495

Cys Ser Arg Cys Lys Ser Gly Phe Phe Asn Leu Gln Glu Asp Asn Trp
            500                 505                 510

Lys Gly Cys Asp Glu Cys Phe Cys Ser Gly Val Ser Asn Arg Cys Gln
        515                 520                 525

Ser Ser Tyr Trp Thr Tyr Gly Lys Ile Gln Asp Met Ser Gly Trp Tyr
    530                 535                 540

Leu Thr Asp Leu Pro Gly Arg Ile Arg Val Ala Pro Gln Gln Asp Asp
545                 550                 555                 560

Leu Asp Ser Pro Gln Gln Ile Ser Ile Ser Asn Ala Glu Ala Arg Gln
                565                 570                 575

Ala Leu Pro His Ser Tyr Tyr Trp Ser Ala Pro Ala Pro Tyr Leu Gly
            580                 585                 590

Asn Lys Leu Pro Ala Val Gly Gly Gln Leu Thr Phe Thr Ile Ser Tyr
        595                 600                 605

Asp Leu Glu Glu Glu Glu Glu Asp Thr Glu Arg Val Leu Gln Leu Met
    610                 615                 620

Ile Ile Leu Glu Gly Asn Asp Leu Ser Ile Ser Thr Ala Gln Asp Glu
625                 630                 635                 640

Val Tyr Leu His Pro Ser Glu Glu His Thr Asn Val Leu Leu Leu Lys
                645                 650                 655

Glu Glu Ser Phe Thr Ile His Gly Thr His Phe Pro Val Arg Arg Lys
            660                 665                 670

Glu Phe Met Thr Val Leu Ala Asn Leu Lys Arg Val Leu Leu Gln Ile
        675                 680                 685

Thr Tyr Ser Phe Gly Met Asp Ala Ile Phe Arg Leu Ser Ser Val Asn
    690                 695                 700

Leu Glu Ser Ala Val Ser Tyr Pro Thr Asp Gly Ser Ile Ala Ala Ala
705                 710                 715                 720

Val Glu Val Cys Gln Cys Pro Pro Gly Tyr Thr Gly Ser Ser Cys Glu
                725                 730                 735

Ser Cys Trp Pro Arg His Arg Arg Val Asn Gly Thr Ile Phe Gly Gly
            740                 745                 750

Ile Cys Glu Pro Cys Gln Cys Phe Gly His Ala Glu Ser Cys Asp Asp
        755                 760                 765

Val Thr Gly Glu Cys Leu Asn Cys Lys Asp His Thr Gly Gly Pro Tyr
    770                 775                 780

Cys Asp Lys Cys Leu Pro Gly Phe Tyr Gly Glu Pro Thr Lys Gly Thr
785                 790                 795                 800

Ser Glu Asp Cys Gln Pro Cys Ala Cys Pro Leu Asn Ile Pro Ser Asn
                805                 810                 815

Asn Phe Ser Pro Thr Cys His Leu Asp Arg Ser Leu Gly Leu Ile Cys
            820                 825                 830

Asp Gly Cys Pro Val Gly Tyr Thr Gly Pro Arg Cys Glu Arg Cys Ala
        835                 840                 845

Glu Gly Tyr Phe Gly Gln Pro Ser Val Pro Gly Gly Ser Cys Gln Pro
    850                 855                 860
```

-continued

```
Cys Gln Cys Asn Asp Asn Leu Asp Phe Ser Ile Pro Gly Ser Cys Asp
865                 870                 875                 880

Ser Leu Ser Gly Ser Cys Leu Ile Cys Lys Pro Gly Thr Thr Gly Arg
                885                 890                 895

Tyr Cys Glu Leu Cys Ala Asp Gly Tyr Phe Gly Asp Ala Val Asp Ala
            900                 905                 910

Lys Asn Cys Gln Pro Cys Arg Cys Asn Ala Gly Gly Ser Phe Ser Glu
        915                 920                 925

Val Cys His Ser Gln Thr Gly Gln Cys Glu Cys Arg Ala Asn Val Gln
    930                 935                 940

Gly Gln Arg Cys Asp Lys Cys Lys Ala Gly Thr Phe Gly Leu Gln Ser
945                 950                 955                 960

Ala Arg Gly Cys Val Pro Cys Asn Cys Asn Ser Phe Gly Ser Lys Ser
                965                 970                 975

Phe Asp Cys Glu Glu Ser Gly Gln Cys Trp Cys Gln Pro Gly Val Thr
            980                 985                 990

Gly Lys Lys Cys Asp Arg Cys Ala  His Gly Tyr Phe Asn  Phe Gln Glu
        995                 1000                1005

Gly Gly  Cys Thr Ala Cys Glu  Cys Ser His Leu Gly  Asn Asn Cys
    1010                1015                1020

Asp Pro  Lys Thr Gly Arg Cys  Ile Cys Pro Pro Asn  Thr Ile Gly
    1025                1030                1035

Glu Lys  Cys Ser Lys Cys Ala  Pro Asn Thr Trp Gly  His Ser Ile
    1040                1045                1050

Thr Thr  Gly Cys Lys Ala Cys  Asn Cys Ser Thr Val  Gly Ser Leu
    1055                1060                1065

Asp Phe  Gln Cys Asn Val Asn  Thr Gly Gln Cys Asn  Cys His Pro
    1070                1075                1080

Lys Phe  Ser Gly Ala Lys Cys  Thr Glu Cys Ser Arg  Gly His Trp
    1085                1090                1095

Asn Tyr  Pro Arg Cys Asn Leu  Cys Asp Cys Phe Leu  Pro Gly Thr
    1100                1105                1110

Asp Ala  Thr Thr Cys Asp Ser  Glu Thr Lys Lys Cys  Ser Cys Ser
    1115                1120                1125

Asp Gln  Thr Gly Gln Cys Thr  Cys Lys Val Asn Val  Glu Gly Ile
    1130                1135                1140

His Cys  Asp Arg Cys Arg Pro  Gly Lys Phe Gly Leu  Asp Ala Lys
    1145                1150                1155

Asn Pro  Leu Gly Cys Ser Ser  Cys Tyr Cys Phe Gly  Thr Thr Thr
    1160                1165                1170

Gln Cys  Ser Glu Ala Lys Gly  Leu Ile Arg Thr Trp  Val Thr Leu
    1175                1180                1185

Lys Ala  Glu Gln Thr Ile Leu  Pro Leu Val Asp Glu  Ala Leu Gln
    1190                1195                1200

His Thr  Thr Thr Lys Gly Ile  Val Phe Gln His Pro  Glu Ile Val
    1205                1210                1215

Ala His  Met Asp Leu Met Arg  Glu Asp Leu His Leu  Glu Pro Phe
    1220                1225                1230

Tyr Trp  Lys Leu Pro Glu Gln  Phe Glu Gly Lys Lys  Leu Met Ala
    1235                1240                1245

Tyr Gly  Gly Lys Leu Lys Tyr  Ala Ile Tyr Phe Glu  Ala Arg Glu
    1250                1255                1260

Glu Thr  Gly Phe Ser Thr Tyr  Asn Pro Gln Val Ile  Ile Arg Gly
```

```
    1265                1270                1275

Gly Thr  Pro Thr His Ala Arg  Ile Ile Val Arg His  Met Ala Ala
    1280                1285                1290

Pro Leu  Ile Gly Gln Leu Thr  Arg His Glu Ile Glu  Met Thr Glu
    1295                1300                1305

Lys Glu  Trp Lys Tyr Tyr Gly  Asp Asp Pro Arg Val  His Arg Thr
    1310                1315                1320

Val Thr  Arg Glu Asp Phe Leu  Asp Ile Leu Tyr Asp  Ile His Tyr
    1325                1330                1335

Ile Leu  Ile Lys Ala Thr Tyr  Gly Asn Phe Met Arg  Gln Ser Arg
    1340                1345                1350

Ile Ser  Glu Ile Ser Met Glu  Val Ala Glu Gln Gly  Arg Gly Thr
    1355                1360                1365

Thr Met  Thr Pro Pro Ala Asp  Leu Ile Glu Lys Cys  Asp Cys Pro
    1370                1375                1380

Leu Gly  Tyr Ser Gly Leu Ser  Cys Glu Ala Cys Leu  Pro Gly Phe
    1385                1390                1395

Tyr Arg  Leu Arg Ser Gln Pro  Gly Gly Arg Thr Pro  Gly Pro Thr
    1400                1405                1410

Leu Gly  Thr Cys Val Pro Cys  Gln Cys Asn Gly His  Ser Ser Leu
    1415                1420                1425

Cys Asp  Pro Glu Thr Ser Ile  Cys Gln Asn Cys Gln  His His Thr
    1430                1435                1440

Ala Gly  Asp Phe Cys Glu Arg  Cys Ala Leu Gly Tyr  Tyr Gly Ile
    1445                1450                1455

Val Lys  Gly Leu Pro Asn Asp  Cys Gln Gln Cys Ala  Cys Pro Leu
    1460                1465                1470

Ile Ser  Ser Ser Asn Asn Phe  Ser Pro Ser Cys Val  Ala Glu Gly
    1475                1480                1485

Leu Asp  Asp Tyr Arg Cys Thr  Ala Cys Pro Arg Gly  Tyr Glu Gly
    1490                1495                1500

Gln Tyr  Cys Glu Arg Cys Ala  Pro Gly Tyr Thr Gly  Ser Pro Gly
    1505                1510                1515

Asn Pro  Gly Gly Ser Cys Gln  Glu Cys Glu Cys Asp  Pro Tyr Gly
    1520                1525                1530

Ser Leu  Pro Val Pro Cys Asp  Pro Val Thr Gly Phe  Cys Thr Cys
    1535                1540                1545

Arg Pro  Gly Ala Thr Gly Arg  Lys Cys Asp Gly Cys  Lys His Trp
    1550                1555                1560

His Ala  Arg Glu Gly Trp Glu  Cys Val Phe Cys Gly  Asp Glu Cys
    1565                1570                1575

Thr Gly  Leu Leu Leu Gly Asp  Leu Ala Arg Leu Glu  Gln Met Val
    1580                1585                1590

Met Ser  Ile Asn Leu Thr Gly  Pro Leu Pro Ala Pro  Tyr Lys Met
    1595                1600                1605

Leu Tyr  Gly Leu Glu Asn Met  Thr Gln Glu Leu Lys  His Leu Leu
    1610                1615                1620

Ser Pro  Gln Arg Ala Pro Glu  Arg Leu Ile Gln Leu  Ala Glu Gly
    1625                1630                1635

Asn Leu  Asn Thr Leu Val Thr  Glu Met Asn Glu Leu  Leu Thr Arg
    1640                1645                1650

Ala Thr  Lys Val Thr Ala Asp  Gly Glu Gln Thr Gly  Gln Asp Ala
    1655                1660                1665
```

```
Glu Arg Thr Asn Thr Arg Ala Lys Ser Leu Gly Glu Phe Ile Lys
    1670                1675                1680

Glu Leu Ala Arg Asp Ala Glu Ala Val Asn Glu Lys Ala Ile Lys
    1685                1690                1695

Leu Asn Glu Thr Leu Gly Thr Arg Asp Glu Ala Phe Glu Arg Asn
    1700                1705                1710

Leu Glu Gly Leu Gln Lys Glu Ile Asp Gln Met Ile Lys Glu Leu
    1715                1720                1725

Arg Arg Lys Asn Leu Glu Thr Gln Lys Glu Ile Ala Glu Asp Glu
    1730                1735                1740

Leu Val Ala Ala Glu Ala Leu Leu Lys Lys Val Lys Lys Leu Phe
    1745                1750                1755

Gly Glu Ser Arg Gly Glu Asn Glu Glu Met Glu Lys Asp Leu Arg
    1760                1765                1770

Glu Lys Leu Ala Asp Tyr Lys Asn Lys Val Asp Asp Ala Trp Asp
    1775                1780                1785

Leu Leu Arg Glu Ala Thr Asp Lys Ile Arg Glu Ala Asn Arg Leu
    1790                1795                1800

Phe Ala Val Asn Gln Lys Asn Met Thr Ala Leu Glu Lys Lys Lys
    1805                1810                1815

Glu Ala Val Glu Ser Gly Lys Arg Gln Ile Glu Asn Thr Leu Lys
    1820                1825                1830

Glu Gly Asn Asp Ile Leu Asp Glu Ala Asn Arg Leu Ala Asp Glu
    1835                1840                1845

Ile Asn Ser Ile Ile Asp Tyr Val Glu Asp Ile Gln Thr Lys Leu
    1850                1855                1860

Pro Pro Met Ser Glu Glu Leu Asn Asp Lys Ile Asp Asp Leu Ser
    1865                1870                1875

Gln Glu Ile Lys Asp Arg Lys Leu Ala Glu Lys Val Ser Gln Ala
    1880                1885                1890

Glu Ser His Ala Ala Gln Leu Asn Asp Ser Ser Ala Val Leu Asp
    1895                1900                1905

Gly Ile Leu Asp Glu Ala Lys Asn Ile Ser Phe Asn Ala Thr Ala
    1910                1915                1920

Ala Phe Lys Ala Tyr Ser Asn Ile Lys Asp Tyr Ile Asp Glu Ala
    1925                1930                1935

Glu Lys Val Ala Lys Glu Ala Lys Asp Leu Ala His Glu Ala Thr
    1940                1945                1950

Lys Leu Ala Thr Gly Pro Arg Gly Leu Leu Lys Glu Asp Ala Lys
    1955                1960                1965

Gly Cys Leu Gln Lys Ser Phe Arg Ile Leu Asn Glu Ala Lys Lys
    1970                1975                1980

Leu Ala Asn Asp Val Lys Glu Asn Glu Asp His Leu Asn Gly Leu
    1985                1990                1995

Lys Thr Arg Ile Glu Asn Ala Asp Ala Arg Asn Gly Asp Leu Leu
    2000                2005                2010

Arg Thr Leu Asn Asp Thr Leu Gly Lys Leu Ser Ala Ile Pro Asn
    2015                2020                2025

Asp Thr Ala Ala Lys Leu Gln Ala Val Lys Asp Lys Ala Arg Gln
    2030                2035                2040

Ala Asn Asp Thr Ala Lys Asp Val Leu Ala Gln Ile Thr Glu Leu
    2045                2050                2055
```

```
His Gln  Asn Leu Asp Gly Leu  Lys Lys Asn Tyr Asn  Lys Leu Ala
    2060                 2065                 2070

Asp Ser  Val Ala Lys Thr Asn  Ala Val Val Lys Asp  Pro Ser Lys
    2075                 2080                 2085

Asn Lys  Ile Ile Ala Asp Ala  Asp Ala Thr Val Lys  Asn Leu Glu
    2090                 2095                 2100

Gln Glu  Ala Asp Arg Leu Ile  Asp Lys Leu Lys Pro  Ile Lys Glu
    2105                 2110                 2115

Leu Glu  Asp Asn Leu Lys Lys  Asn Ile Ser Glu Ile  Lys Glu Leu
    2120                 2125                 2130

Ile Asn  Gln Ala Arg Lys Gln  Ala Asn Ser Ile Lys  Val Ser Val
    2135                 2140                 2145

Ser Ser  Gly Gly Asp Cys Ile  Arg Thr Tyr Lys Pro  Glu Ile Lys
    2150                 2155                 2160

Lys Gly  Ser Tyr Asn Asn Ile  Val Val Asn Val Lys  Thr Ala Val
    2165                 2170                 2175

Ala Asp  Asn Leu Leu Phe Tyr  Leu Gly Ser Ala Lys  Phe Ile Asp
    2180                 2185                 2190

Phe Leu  Ala Ile Glu Met Arg  Lys Gly Lys Val Ser  Phe Leu Trp
    2195                 2200                 2205

Asp Val  Gly Ser Gly Val Gly  Arg Val Glu Tyr Pro  Asp Leu Thr
    2210                 2215                 2220

Ile Asp  Asp Ser Tyr Trp Tyr  Arg Ile Val Ala Ser  Arg Thr Gly
    2225                 2230                 2235

Arg Asn  Gly Thr Ile Ser Val  Arg Ala Leu Asp Gly  Pro Lys Ala
    2240                 2245                 2250

Ser Ile  Val Pro Ser Thr His  His Ser Thr Ser Pro  Pro Gly Tyr
    2255                 2260                 2265

Thr Ile  Leu Asp Val Asp Ala  Asn Ala Met Leu Phe  Val Gly Gly
    2270                 2275                 2280

Leu Thr  Gly Lys Leu Lys Lys  Ala Asp Ala Val Arg  Val Ile Thr
    2285                 2290                 2295

Phe Thr  Gly Cys Met Gly Glu  Thr Tyr Phe Asp Asn  Lys Pro Ile
    2300                 2305                 2310

Gly Leu  Trp Asn Phe Arg Glu  Lys Glu Gly Asp Cys  Lys Gly Cys
    2315                 2320                 2325

Thr Val  Ser Pro Gln Val Glu  Asp Ser Glu Gly Thr  Ile Gln Phe
    2330                 2335                 2340

Asp Gly  Glu Gly Tyr Ala Leu  Val Ser Arg Pro Ile  Arg Trp Tyr
    2345                 2350                 2355

Pro Asn  Ile Ser Thr Val Met  Phe Lys Phe Arg Thr  Phe Ser Ser
    2360                 2365                 2370

Ser Ala  Leu Leu Met Tyr Leu  Ala Thr Arg Asp Leu  Arg Asp Phe
    2375                 2380                 2385

Met Ser  Val Glu Leu Thr Asp  Gly His Ile Lys Val  Ser Tyr Asp
    2390                 2395                 2400

Leu Gly  Ser Gly Met Ala Ser  Val Val Ser Asn Gln  Asn His Asn
    2405                 2410                 2415

Asp Gly  Lys Trp Lys Ser Phe  Thr Leu Ser Arg Ile  Gln Lys Gln
    2420                 2425                 2430

Ala Asn  Ile Ser Ile Val Asp  Ile Asp Thr Asn Gln  Glu Glu Asn
    2435                 2440                 2445

Ile Ala  Thr Ser Ser Ser Gly  Asn Asn Phe Gly Leu  Asp Leu Lys
```

-continued

```
    2450                2455                2460

Ala Asp  Asp Lys Ile Tyr Phe  Gly Gly Leu Pro Thr  Leu Arg Asn
    2465                2470                2475

Leu Ser  Met Lys Ala Arg Pro  Glu Val Asn Leu Lys  Lys Tyr Ser
    2480                2485                2490

Gly Cys  Leu Lys Asp Ile Glu  Ile Ser Arg Thr Pro  Tyr Asn Ile
    2495                2500                2505

Leu Ser  Ser Pro Asp Tyr Val  Gly Val Thr Lys Gly  Cys Ser Leu
    2510                2515                2520

Glu Asn  Val Tyr Thr Val Ser  Phe Pro Lys Pro Gly  Phe Val Glu
    2525                2530                2535

Leu Ser  Pro Val Pro Ile Asp  Val Gly Thr Glu Ile  Asn Leu Ser
    2540                2545                2550

Phe Ser  Thr Lys Asn Glu Ser  Gly Ile Ile Leu Leu  Gly Ser Gly
    2555                2560                2565

Gly Thr  Pro Ala Pro Pro Arg  Arg Lys Arg Arg Gln  Thr Gly Gln
    2570                2575                2580

Ala Tyr  Tyr Ala Ile Leu Leu  Asn Arg Gly Arg Leu  Glu Val His
    2585                2590                2595

Leu Ser  Thr Gly Ala Arg Thr  Met Arg Lys Ile Val  Ile Arg Pro
    2600                2605                2610

Glu Pro  Asn Leu Phe His Asp  Gly Arg Glu His Ser  Val His Val
    2615                2620                2625

Glu Arg  Thr Arg Gly Ile Phe  Thr Val Gln Val Asp  Glu Asn Arg
    2630                2635                2640

Arg Tyr  Met Gln Asn Leu Thr  Val Glu Gln Pro Ile  Glu Val Lys
    2645                2650                2655

Lys Leu  Phe Val Gly Gly Ala  Pro Pro Glu Phe Gln  Pro Ser Pro
    2660                2665                2670

Leu Arg  Asn Ile Pro Pro Phe  Glu Gly Cys Ile Trp  Asn Leu Val
    2675                2680                2685

Ile Asn  Ser Val Pro Met Asp  Phe Ala Arg Pro Val  Ser Phe Lys
    2690                2695                2700

Asn Ala  Asp Ile Gly Arg Cys  Ala His Gln Lys Leu  Arg Glu Asp
    2705                2710                2715

Glu Asp  Gly Ala Ala Pro Ala  Glu Ile Val Ile Gln  Pro Glu Pro
    2720                2725                2730

Val Pro  Thr Pro Ala Phe Pro  Thr Pro Thr Pro Val  Leu Thr His
    2735                2740                2745

Gly Pro  Cys Ala Ala Glu Ser  Glu Pro Ala Leu Leu  Ile Gly Ser
    2750                2755                2760

Lys Gln  Phe Gly Leu Ser Arg  Asn Ser His Ile Ala  Ile Ala Phe
    2765                2770                2775

Asp Asp  Thr Lys Val Lys Asn  Arg Leu Thr Ile Glu  Leu Glu Val
    2780                2785                2790

Arg Thr  Glu Ala Glu Ser Gly  Leu Leu Phe Tyr Met  Ala Arg Ile
    2795                2800                2805

Asn His  Ala Asp Phe Ala Thr  Val Gln Leu Arg Asn  Gly Leu Pro
    2810                2815                2820

Tyr Phe  Ser Tyr Asp Leu Gly  Ser Gly Asp Thr His  Thr Met Ile
    2825                2830                2835

Pro Thr  Lys Ile Asn Asp Gly  Gln Trp His Lys Ile  Lys Ile Met
    2840                2845                2850
```

```
Arg Ser  Lys Gln Glu Gly Ile  Leu Tyr Val Asp Gly  Ala Ser Asn
    2855                 2860                 2865

Arg Thr  Ile Ser Pro Lys Lys  Ala Asp Ile Leu Asp  Val Val Gly
    2870                 2875                 2880

Met Leu  Tyr Val Gly Gly Leu  Pro Ile Asn Tyr Thr  Thr Arg Arg
    2885                 2890                 2895

Ile Gly  Pro Val Thr Tyr Ser  Ile Asp Gly Cys Val  Arg Asn Leu
    2900                 2905                 2910

His Met  Ala Glu Ala Pro Ala  Asp Leu Glu Gln Pro  Thr Ser Ser
    2915                 2920                 2925

Phe His  Val Gly Thr Cys Phe  Ala Asn Ala Gln Arg  Gly Thr Tyr
    2930                 2935                 2940

Phe Asp  Gly Thr Gly Phe Ala  Lys Ala Val Gly Gly  Phe Lys Val
    2945                 2950                 2955

Gly Leu  Asp Leu Leu Val Glu  Phe Glu Phe Arg Thr  Thr Thr Thr
    2960                 2965                 2970

Thr Gly  Val Leu Leu Gly Ile  Ser Ser Gln Lys Met  Asp Gly Met
    2975                 2980                 2985

Gly Ile  Glu Met Ile Asp Glu  Lys Leu Met Phe His  Val Asp Asn
    2990                 2995                 3000

Gly Ala  Gly Arg Phe Thr Ala  Val Tyr Asp Ala Gly  Val Pro Gly
    3005                 3010                 3015

His Leu  Cys Asp Gly Gln Trp  His Lys Val Thr Ala  Asn Lys Ile
    3020                 3025                 3030

Lys His  Arg Ile Glu Leu Thr  Val Asp Gly Asn Gln  Val Glu Ala
    3035                 3040                 3045

Gln Ser  Pro Asn Pro Ala Ser  Thr Ser Ala Asp Thr  Asn Asp Pro
    3050                 3055                 3060

Val Phe  Val Gly Gly Phe Pro  Asp Asp Leu Lys Gln  Phe Gly Leu
    3065                 3070                 3075

Thr Thr  Ser Ile Pro Phe Arg  Gly Cys Ile Arg Ser  Leu Lys Leu
    3080                 3085                 3090

Thr Lys  Gly Thr Gly Lys Pro  Leu Glu Val Asn Phe  Ala Lys Ala
    3095                 3100                 3105

Leu Glu  Leu Arg Gly Val Gln  Pro Val Ser Cys Pro  Ala Asn
    3110                 3115                 3120


<210> SEQ ID NO 3
<211> LENGTH: 480
<212> TYPE: PRT
<213> ORGANISM: Homo sapiens

<400> SEQUENCE: 3

Met Ala Arg Phe Pro Lys Ala Asp Leu Ala Ala Ala Gly Val Met Leu
1               5                   10                  15

Leu Cys His Phe Phe Thr Asp Gln Phe Gln Phe Ala Asp Gly Lys Pro
            20                  25                  30

Gly Asp Gln Ile Leu Asp Trp Gln Tyr Gly Val Thr Gln Ala Phe Pro
        35                  40                  45

His Thr Glu Glu Glu Val Glu Val Asp Ser His Ala Tyr Ser His Arg
    50                  55                  60

Trp Lys Arg Asn Leu Asp Phe Leu Lys Ala Val Asp Thr Asn Arg Ala
65                  70                  75                  80

Ser Val Gly Gln Asp Ser Pro Glu Pro Arg Ser Phe Thr Asp Leu Leu
```

-continued

```
                85                  90                  95

Leu Asp Asp Gly Gln Asp Asn Asn Thr Gln Ile Glu Arg Val Asn Leu
            100                 105                 110

Ser Phe Asp Phe Pro Phe Tyr Gly His Phe Leu Arg Glu Ile Thr Val
        115                 120                 125

Ala Thr Gly Gly Phe Ile Tyr Thr Gly Glu Val Val His Arg Met Leu
    130                 135                 140

Thr Ala Thr Gln Tyr Ile Ala Pro Leu Met Ala Asn Phe Asp Pro Ser
145                 150                 155                 160

Val Ser Arg Asn Ser Thr Val Arg Tyr Phe Asp Asn Gly Thr Ala Leu
                165                 170                 175

Val Val Gln Trp Asp His Val His Leu Gln Asp Asn Tyr Asn Leu Gly
            180                 185                 190

Ser Phe Thr Phe Gln Ala Thr Leu Leu Met Asp Gly Arg Ile Ile Phe
        195                 200                 205

Gly Tyr Lys Glu Ile Pro Val Leu Val Thr Gln Ile Ser Ser Thr Asn
    210                 215                 220

His Pro Val Lys Val Gly Leu Ser Asp Ala Phe Val Val Val His Arg
225                 230                 235                 240

Ile Gln Gln Ile Pro Asn Val Arg Arg Arg Thr Ile Tyr Glu Tyr His
                245                 250                 255

Arg Val Glu Leu Gln Met Ser Lys Ile Thr Asn Ile Ser Ala Val Glu
            260                 265                 270

Met Thr Pro Leu Pro Thr Cys Leu Gln Phe Asn Arg Cys Gly Pro Cys
        275                 280                 285

Val Ser Ser Gln Ile Gly Phe Asn Cys Ser Trp Cys Ser Lys Leu Gln
    290                 295                 300

Arg Cys Ser Ser Gly Phe Asp Arg His Arg Gln Asp Trp Val Asp Ser
305                 310                 315                 320

Gly Cys Pro Glu Glu Ser Lys Glu Lys Met Cys Glu Asn Thr Glu Pro
                325                 330                 335

Val Glu Thr Ser Ser Arg Thr Thr Thr Thr Val Gly Ala Thr Thr Thr
            340                 345                 350

Gln Phe Arg Val Leu Thr Thr Thr Arg Arg Ala Val Thr Ser Gln Phe
        355                 360                 365

Pro Thr Ser Leu Pro Thr Glu Asp Asp Thr Lys Ile Ala Leu His Leu
    370                 375                 380

Lys Asp Asn Gly Ala Ser Thr Asp Asp Ser Ala Ala Glu Lys Lys Gly
385                 390                 395                 400

Gly Thr Leu His Ala Gly Leu Ile Ile Gly Ile Leu Ile Leu Val Leu
                405                 410                 415

Ile Val Ala Thr Ala Ile Leu Val Thr Val Tyr Met Tyr His His Pro
            420                 425                 430

Thr Ser Ala Ala Ser Ile Phe Phe Ile Glu Arg Arg Pro Ser Arg Trp
        435                 440                 445

Pro Ala Met Lys Phe Arg Arg Gly Ser Gly His Pro Ala Tyr Ala Glu
    450                 455                 460

Val Glu Pro Val Gly Glu Lys Glu Gly Phe Ile Val Ser Glu Gln Cys
465                 470                 475                 480
```